United States Patent
Miller

(10) Patent No.: US 9,949,675 B2
(45) Date of Patent: Apr. 24, 2018

(54) NONINVASIVE BLOOD MEASUREMENT PLATFORM

(71) Applicant: Convergence Biometrics, LLC, Morgan, UT (US)

(72) Inventor: David R. Miller, Morgan, UT (US)

(73) Assignee: Convergence Biometrics, LLC, Morgan, UT (US)

( * ) Notice: Subject to any disclaimer, the term of this patent is extended or adjusted under 35 U.S.C. 154(b) by 216 days.

(21) Appl. No.: 14/059,316

(22) Filed: Oct. 21, 2013

(65) Prior Publication Data

US 2014/0114151 A1  Apr. 24, 2014

Related U.S. Application Data

(60) Provisional application No. 61/716,411, filed on Oct. 19, 2012.

(51) Int. Cl.
| | |
|---|---|
| *A61B 5/1455* | (2006.01) |
| *A61B 5/1477* | (2006.01) |
| *A61B 5/145* | (2006.01) |
| *A61B 5/00* | (2006.01) |

(52) U.S. Cl.
CPC .......... *A61B 5/1455* (2013.01); *A61B 5/1477* (2013.01); *A61B 5/14532* (2013.01); *A61B 5/14546* (2013.01); *A61B 5/14551* (2013.01); *A61B 5/6826* (2013.01)

(58) Field of Classification Search
CPC .............. A61B 5/1455; A61B 5/14551; A61B 5/14532; A61B 5/14552; A61B 5/6826
See application file for complete search history.

(56) References Cited

U.S. PATENT DOCUMENTS

| | | | | |
|---|---|---|---|---|
| 4,859,056 A | * | 8/1989 | Prosser | A61B 5/14551 356/41 |
| 5,515,847 A | * | 5/1996 | Braig | A61B 5/14532 600/316 |
| 6,334,065 B1 | * | 12/2001 | Al-Ali | A61B 5/746 600/323 |
| 2004/0220484 A1 | * | 11/2004 | Steuer | A61B 5/0275 600/505 |
| 2005/0192493 A1 | * | 9/2005 | Wuori | A61B 5/1455 600/322 |

* cited by examiner

*Primary Examiner* — Eric Winakur
*Assistant Examiner* — Marjan Fardanesh
(74) *Attorney, Agent, or Firm* — Mohr Intellectual Property Law Solutions, P.C.

(57) ABSTRACT

A noninvasive blood measurement platform may be used to determine the amounts of various constituents of the blood based on the bulk absorption characteristics of the blood. The platform may measure bulk absorption of energy such as, a broad-spectrum light, to determine maximum and minimum blood volumes. The platform may measure bulk absorption of energy at the maximum and minimum blood volumes. The bulk absorption measurements may be transformed using a transformation operation to determine bulk absorption characteristics in terms of frequency and/or wavelength. A time-varying component of the bulk absorption characteristics may be derived by comparing the bulk absorption characteristics at the maximum blood volume to the bulk absorption characteristics at the minimum blood volume. Multivariate analysis may be performed on the time-varying component to determine the amount of the one or more constituents of the blood.

7 Claims, 12 Drawing Sheets

NONINVASIVE BLOOD MEASUREMENT PLATFORM

CROSS-REFERENCE TO RELATED APPLICATIONS

This application claims priority to U.S. Provisional Patent Application No. 61/716,411, entitled "Non-Invasive Blood Measurement Platform," filed Oct. 19, 2012, and which is hereby incorporated by reference in its entirety.

BACKGROUND

The medical practice utilizes a number of procedures and indicators to assess a patient's condition. Some medical diagnosis and treatment practices require invasive procedures for accurate treatment. For instance, a common invasive procedure involves the measurement of blood glucose, wherein an invasive blood glucose measurement device can be used to prick a patient's finger, collect a blood sample, and measure the blood glucose level externally. Other types of medical diagnosis and treatments may be performed non-invasively. For example, pulse oximetry is a non-invasive method for monitoring a patient's O2 saturation. To measure pulse oximetry, a photodetector sensor is placed on a thin part of the patient's body, usually a fingertip or earlobe, or in the case of an infant, across a foot. Light is passed through the patient to a photodetector. An analysis of the light can be used to determine the patient's oxygen saturation. There is a growing desire within the medical community to move away from invasive procedures and develop instruments to assess and monitor functions continuously and in real time in a non-invasive and non-obtrusive way. Non-invasive monitors reduce the need for long hospitalization periods. Non-invasive monitors also reduce healthcare costs and improve patient comfort and safety. In recent years, electrocardiograms, intermittent blood pressure monitors and pulse oximeters have been used to non-invasively monitor patients' blood pressure and/or oxygen levels. Unfortunately, these devices still provide an incomplete picture of a patient's health status.

DETAILED DESCRIPTION

Figure 1:
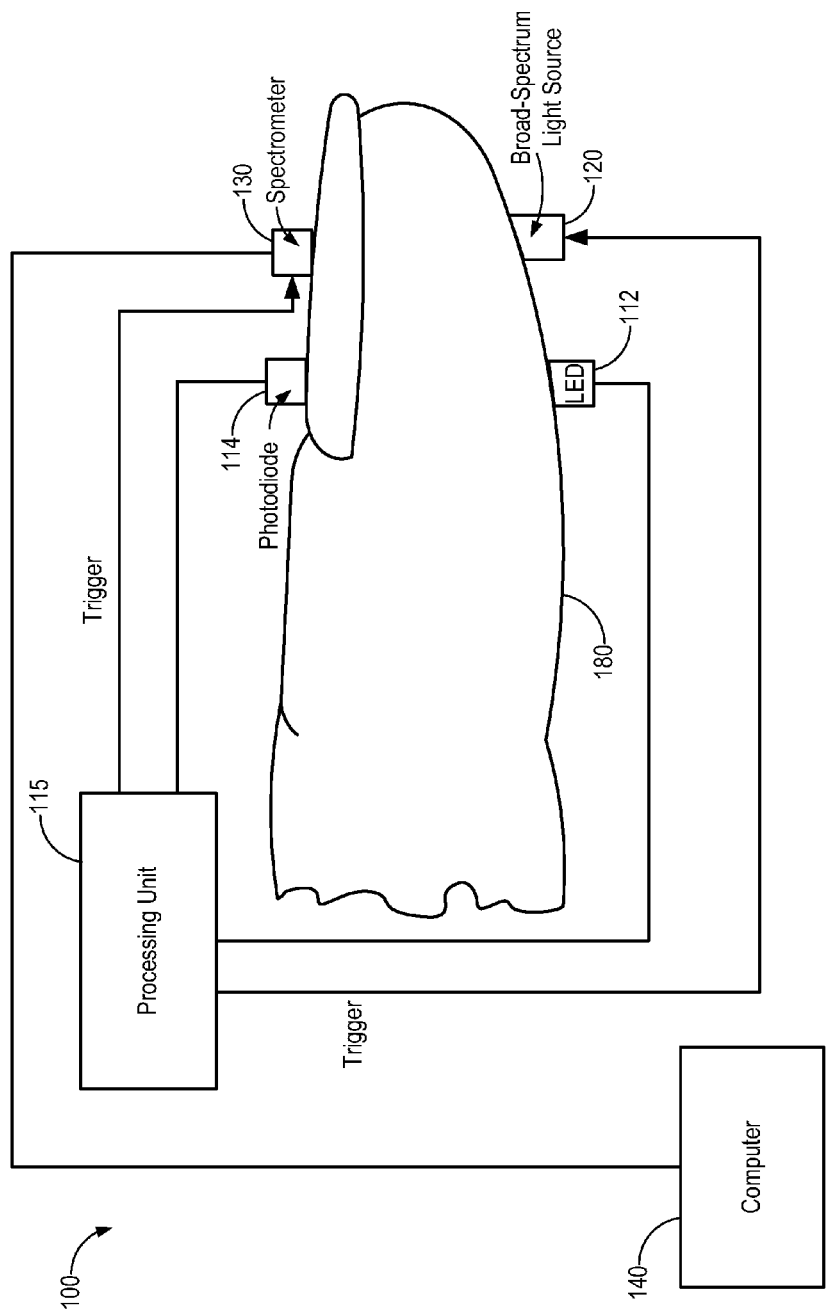
FIG. 1 is a schematic diagram of an apparatus for noninvasive blood measurement in accordance with an example.

Information about health and numerous medical conditions of a subject such as an animal or human-being may be determined by analyzing constituents of the subject's blood. The blood may be analyzed by drawing it from a subject and examining the drawn blood to determine its constituents. Unfortunately, drawing blood may be painful and unpleasant for the subject. Additionally, the examination of blood only allows for a single or discrete measurement to determine a subject's blood constituents. The analysis of blood draws limits the measurement of the blood constituents to only periodically taking measurements or spot checking the subject's blood constituents.

Blood may instead be analyzed noninvasively without needing to draw blood or cause pain to the subject. Additionally, non-invasive monitoring, measuring, and analysis of blood enable a larger number of measurements to be taken relative to the use of invasive measurements. In some embodiments, continuous measurements can be taken. The large number of measurements can provide additional information, such as the use of trend analysis in analyzing and/or determining changes in the constituents (i.e. blood constituents) of the subject's body over time.

A typical location for performing non-invasive measurements is a relatively thin location of the subject's body, such as the subject's finger. The subject's finger is comprised of multiple different constituents such as blood, tissue, water, bone, and so forth. Different constituents of the finger may absorb, scatter, or reflect different quantities of electromagnetic radiation (EM) that are radiated into the finger. For instance, EM can include ultraviolet (UV) light, visible light, infrared (IR) light, terahertz waves, microwaves, or other desired portions of the electromagnetic spectrum. EM signals at different frequencies may be absorbed, scattered, and/or reflected in different ways by the constituents. The constituents of a subject's body may be identified noninvasively based on multivariate analysis performed on a constituent's bulk absorption spectrums of the EM radiation. Additionally, sub-components or sub-constituents of a constituent may also be identified based on the multivariate analysis of the measurements of their bulk absorption spectrum, such as the white blood cells, red blood cells, platelets, plasma, agglutination, antibodies, and other desired sub-constituents. The sub-components or sub-constituents may also include glucose, amino acids, proteins, or another desired constituent or component.

In one embodiment, bulk absorption and/or the measurement of bulk absorption may refer to bulk absorption. In another embodiment, bulk absorption is determined as a function of the scattering and the absorption of energy. Bulk absorption may be calculated as: $\alpha = f(a+s)$, where $\alpha$ is bulk absorption of the energy, a is the absorption of the energy, and s is the scattering of the energy.

In one embodiment, to determine which constituents are present, the amount or level of the constituents, or the trend or change in the level of constituents for a given body or appendage, an orthogonal-hybrid measurement system may be used. The orthogonal-hybrid system can use at least two different energy signals, such as different EM signals or sonic signals, to identify information about the constituents or sub-constituents. When the energy signals are orthogonal, different information can be obtained from each energy signal, thereby providing an aggregate increase in information.

The body's constituents are primarily composed of organic molecules. The organic molecules are typically composed of combinations of hydrogen, nitrogen, oxygen and carbon. While optical spectroscopy can be used to identify different atoms, it can be difficult to spectroscopically identify different types of organic molecules, with their similar atomic makeup. Many organic molecules have similar bulk absorption characteristics to radiated EM energy. In one embodiment an orthogonal-hybrid measurement system can be used to distinguish certain parameters, such as body or appendage components, molecules, blood constituents, body or appendage constituents, sub-components, or sub-constituents.

An orthogonal-hybrid system or a multi-modal system may use multiple energy sources to transmit energy, such as EM signals, to a given body or appendage. Multiple energy detectors can be used to measure or detect the bulk absorption of the energy by the constituents in the subject. For example, an impedance spectrometer or an optical spectrometer can be used to measure the constituents in a given body or appendage.

In one embodiment of an orthogonal-hybrid system, a broad-spectrum light source can emit a broad-spectrum light to the body of a subject and an electrical signal source can emit an electrical signal, such as a radio frequency signal, to the body of the subject. A first energy detector, such as an optical spectrometer, may be used to detect or measure the bulk absorption of the broad-spectrum light. A second energy detector, such as an impedance spectrometer, may be used to detect or measure the impedance of the electrical signal.

A computer processor can be used to calculate spectral characteristics of bulk absorption measurements made by the first energy detector and the spectral characteristics of bulk absorption measurements made by the second energy detector.

In one embodiment, the processor can calculate the spectral characteristics of the bulk absorption measurements in combination or aggregate by correlating the bulk absorption measurements of the first energy detector and the bulk absorption measurements of the second energy detector and aggregating them. In another embodiment, the processor can calculate the bulk absorption measurements of each of the first energy detector and the second energy detector separately.

Orthogonality may be determined from the bulk absorption, impedance, sonic, or other types of measurements taken using a plurality of energy sources and energy detectors. In one embodiment, the bulk absorption measurements can be taken contemporaneously using the plurality of energy sources and energy detectors. In another embodiment, the bulk absorption measurements can be taken sequentially using the plurality of energy sources and energy detectors.

Signals are considered to be mathematically orthogonal when their dot product is zero. In other words, when two orthogonal signals are multiplied together and then integrated, the result is zero. In one example, bulk absorption measurements can be taken contemporaneously using a first energy detector, such as an optical spectrometer, and a second energy detector, such as an impedance spectrometer.

Additionally, reference measurements may also be taken contemporaneously with the bulk absorption measurements, such as a measurement of the subject's pulse, blood oxygen saturation, blood protein levels or other desired types of reference measurements. Alternatively, reference measurements may be a relatively large sample of measurements made prior to the spectrometer measurements. For instance, invasive measurements of blood constituents may be performed for a sample population, such as 50, 100 or more people. For each individual sample, an analysis can then be performed. The analyses for the sample population may then be averaged and used as the reference measurement for non-invasive measurements of the same constituents.

The blood constituent results, as determined from the bulk absorption measurements collected from each energy detector, can be separately compared to the reference measurement(s) to determine how closely the measurements from the energy detectors align with the reference measurements. One statistical means for determining this is by determining a coefficient of variation of the blood constituent results, relative to reference measurements of one or more of the blood constituents. The coefficient of variation can be calculated for the blood constituent results, as determined from bulk absorption measurements taken by each energy detector.

Additionally, the blood constituent results, collected from each energy detector, can be aggregated together and then compared to the reference measurement(s) to determine the coefficient of variation for the blood constituent results. The coefficient of variation can then be compared between the separate blood constituent results and the aggregate blood constituent results. As the coefficient of variation of the aggregate blood constituent results decreases over the coefficient of variation measurements for any of the separate blood constituent results, the degree of orthogonality increases. The greater the amount of orthogonality that exists between different measurements, the more information can be derived from the measurements.

For example, for a given subject an optical spectrometer can be used to take bulk absorption measurements for the subject. Separate bulk absorption measurements can be taken using an impedance spectrometer. At the same time, reference measurements can be taken on the subject using other devices to determine measurements such as blood oxygen level, pulse, or blood protein levels. The blood constituent results from the optical spectrometer and the impedance spectrometer can then each be separately compared to the reference measurements to determine a coefficient of variation for the blood constituent results from the optical spectrometer and the impedance spectrometer, respectively. Additionally, the blood constituent results from the optical spectrometer and the impedance spectrometer can be aggregated together and compared to the reference measurements to determine a coefficient of variation for the aggregated blood constituent results.

In one example, a bulk absorption measurement is taken for a given subject using an energy detector. The data obtained from the bulk absorption measurement can then be analyzed using a multivariate analysis to curve fit the data to a reference curve. The reference curve may be obtained from additional measurements of the subject or prior measurements of a plurality of subjects. This will be further discussed in the proceeding paragraphs.

A statistical analysis can then be performed on the curve fit data to determine blood constituent results for selected or defined blood constituents, such as hemoglobin levels, glucose levels, etc. After the blood constituent results are determined, a coefficient of variation can then be taken for one or more of the selected or defined blood constituents results relative to a reference measurement for the selected or defined blood constituent to determine how closely the outcome of the statistical analysis for each of the selected or defined blood constituents results align with the reference measurements.

If the aggregated blood constituent data have a lower coefficient of variation than the blood constituent measurements from the optical spectrometer and the impedance spectrometer individually, then the blood constituent measurements for the optical spectrometer and the impedance spectrometer can be considered to be orthogonal.

If the measurements from different spectrometer devices are completely orthogonal then there is no correlating and/or overlapping data or information between the measurements, e.g. the data or information collected using each spectrometer is separate or unique. Even when signals are not completely orthogonal, some degree of orthogonality can result in an increase in information obtained from multiple measurements relative to a single measurement. When orthogonal measurement data or information is collected from multiple sources, additional or finer details regarding the constituents may be determined. In one embodiment, the orthogonal data may provide a more detailed representation of the constituent data as a whole as the non-overlapping data collected using one spectrometer may augment the data collected from another spectrometer. Conversely, if the different measurements are not orthogonal, then the data or information from the measurements can be considered to be overlapping or duplicative.

In one example, an orthogonal plane or graph may include an axis comprised of wavelengths or energy radiated from an optical spectrometer and another axis comprising wavelengths or energy radiated from an impedance spectrometer.

The devices or methods used to take the measurements may include acoustic resonance spectroscopy, laser spectroscopy, mass spectroscopy, Raman spectroscopy, thermal spectroscopy, photoelectron spectroscopy, or other desired spectroscopic measurement techniques.

In one embodiment, multiple devices or methods can be used that radiate different wavelengths of EM or acoustic energy. In one embodiment, the information from the different wavelengths can be compared in order to determine the correlation or orthogonality of the information. In one embodiment, when the measurements for constituents are similar or the same at separate or different wavelengths then the degree of accuracy of the measurements is high. In another embodiment, the information or measurements that have a high correlation can occur at harmonic wavelengths. In another embodiment, orthogonality may be used to distinguish different constituents. For example, glucose absorbs energy at 2200 nm and urea absorbs energy at 2150 nm. Using a single type of measurement, it can be difficult to distinguish between the different wavelengths to identify the glucose and urea constituents. By using multiple devices or methods to measure the bulk absorption of energy at 2200 nm and 2150 nm, each constituent may be more readily distinguished from other constituents.

An apparatus for noninvasive blood measurement may emit electromagnetic radiation at a targeted location on the subject, appendage, or extremity and measure bulk absorption at the target and thereby calculate concentrations of a constituent, such as a constituent of blood. The constituent measurement information may be separated or compartmentalized based on the bulk absorption or scattering. In one embodiment, the measurement information can be taken using pulsatile measurements, such as by taking measurements at specified times over a defined period. The measurement information may also be taken continuously, near-continuously, or for a selected number of measurements over a predetermined period.

The target may include any part on the subject, such as a fingertip, finger webbing, an inside of a lip, an ear lobe, and/or the like. The target may include a blood constituent and other non-blood components.

Noise may interfere with bulk absorption measurements and decrease the accuracy and/or precision of the bulk absorption measurements. The noise may include leakage of natural or ambient light into the broad spectrum light source, and electronic noise from electronic signals of various components or devices. The noise may also include interference of the light or energy interacting with non-desired components. For example, if a measurement is desired for a constituent of blood, a non-desired component can include bone, tissue or water. As the non-blood components absorb, reflect, and scatter energy or light emitted into the target it creates noise and/or interference in the signal used to determine the bulk absorption measurements. A signal-to-noise ratio (SNR) or a signal to interference plus noise ratio (SINR) of measurements may be improved by isolating bulk absorption by constituents of the blood constituents from the noise, such as the bulk absorption by the non-blood components. The improved SNR or SINR may allow for more accurate and/or precise identification of the amount (e.g., concentration) of each constituent in the blood.

The amount of blood at the target may vary over time while the amount of non-blood components may remain relatively constant. Measuring bulk absorption for different blood volumes may allow time-varying components (e.g., the blood component) to be isolated from static components (e.g., the non-blood components). The blood volume may be varied due to internal/natural changes resulting from biological processes, such as the cardiac cycle, due to external processes, such as pressure from an inflatable cuff, and/or the like. For example, a first bulk absorption measurement may be performed when blood volume is at a maximum, when the heart has fully compressed, and a second bulk absorption measurement may be performed when blood volume is at a minimum, when the heart is relaxed. At the points of maximum and minimum volume, the rate of change of the volume may be small. In one embodiment, a photoplethysmogram may be used to detect the points of maximum and minimum volume or the volumetric change of a body, appendage, or extremity. For example a photoplethysmogram may be used to detect the volumetric change of the blood in the finger of a subject. In one embodiment, a photoplethysmogram may be used to detect the volume or volumetric change by taking a continuous measurement or by taking a full spectral data set. In one example, the volumetric change of blood in a subject's appendage is measured using a photoplethysmograph by measuring an optical signal in an appendage, such as a finger. Blood is optically denser at selected wavelengths than the surrounding components such as tissue, so when a subject's heart contracts and releases a volume of blood, the amount of blood in a finger increases and decreases, respectively. For a given cardiac cycle, there is a full or complete volumetric change from a minimum volume point to a maximum volume point, with a corresponding change in the bulk absorption measurement of the optical signal.

In an embodiment, a narrow-spectrum light source may emit light in a narrow spectrum at the target, and a narrow-spectrum light detector may measure bulk absorption of the narrow-spectrum light. The narrow-spectrum light source may emit light at a discrete wavelength, such as 650 nm or 940 nm, to measure the pulse oximetry of a subject. In another embodiment, a broad-spectrum light source may emit a broad spectrum of light at a target. A broad-spectrum light detector may measure bulk absorption of the broad spectrum of light. In one example, the broad-spectrum light detector may detect a large number of continuous wavelengths, such as 3000 or more distinct or unique wavelengths of light on a continuous scale.

One advantage of detecting or collecting information on a continuous scale for a selected or defined wavelength range is that it enables the detection of minute or small changes in constituents or analytes. The information collected on a continuous scale may then be analyzed to detect constituents such as hemoglobin, urea, etc. In one embodiment, the broad-spectrum light source may emit a broad light spectrum range from 400 nm to 1500 nm. In another embodiment, the broad light spectrum range may include EM in the visible light spectrum and/or the infrared light spectrum. The broad-spectrum light range used may depend on the components and/or analytes that are to be analyzed. For example, oxygenated hemoglobin and non-oxygenated hemoglobin absorb light at different wavelengths and may require different wavelength or light ranges for detection. In another example, glucose and hemoglobin have the same or similar light bulk absorption characteristic so that one wavelength or light range may be sufficient to measurement data for both parameters. In another embodiment, a broad-spectrum light source may continuously or repeatedly emit light in a broad spectrum at the target, and a broad-spectrum light detector may measure the bulk absorption of the broad-spectrum light.

A point of maximum absorbance on the photoplethysmograph may correspond with a point of maximum volume, and a point of minimum absorbance may correspond with a point of minimum volume. In one embodiment, the maximum and minimum points may be determined based on when a rate of change of the signal exceeds or falls below defined or selected thresholds. Performing a derivative operation can be used to measure the rate of change. Most components in a body part, such as a finger, will typically not change much. For example, the amount of bone, collagen (i.e. skin), water, and other components will not change or will change slowly over time. By performing the derivative operation, these components can be substantially eliminated with respect to the blood, which is changing over time due to the cardiac cycle. By eliminating the signals received from substantially static components within the measurement area, the signal can more accurately reflect the subcomponents in the blood. In one embodiment, this provides a significant improvement in the signal to noise (SNR and/or SINR) of measurements, based on whether a first derivative of the signal is less than a defined or selected predetermined threshold, or the like. In another embodiment, significant improvement in the signal to noise (SNR and/or SINR) of measurements are made by calculating the minimum blood volume points and maximum blood volume points in the measurement data and taking the difference between the minimum blood volume points and maximum blood volume points to subtract out the substantially static components. The difference may be obtained by performing a differentiation or a ratio metric calculation of the points.

In one embodiment, the maximum volume point and the minimum volume point are determined at a relatively stable point in the cardiac cycle. The stable points in the cardiac cycle may be at the apex point and/or the period surrounding the inflection points of the maximum and/or minimum volume points. In one example, the inflection points may remain relatively stable for approximately 20-30 milliseconds. Energy may be emitted continuously from an emitter, such as an optical, electrical, or sonic emitter. The bulk absorption measurements may be limited to the period at or approximate to the inflection points or the maximum and/or minimum volume points.

In another embodiment, a plurality of bulk absorption measurements can be made at the period at or approximate to the inflection points or the maximum and/or minimum volume points. In one embodiment, the SNR and/or SINR are maximized by taking bulk absorption measurements at the maximum volume point and the minimum volume points of the cardiac cycle by determining a maximum rate of change between the maximum volume point and the minimum volume point.

The dicrotic notch is a downward or upward deflection in the arterial pulse tracing or pressure contour immediately following the closure of the semilunar valves and preceding the dicrotic wave and corresponding to the transient increase in aortic pressure upon closure of the aortic valve. The dicrotic notch or incisures may create false maximum and minimum points as there is a minor increase and decrease in arterial pulse. A subject's respiration may also alter the maximum and/or minimum points in the bulk absorption measurements by stretching or compressing the measured cardiac cycle due to respiration. This alteration can result in additional error. In one embodiment, the maximum and minimum points may be determined based on pulse detection and characterization and accounting for and/or filtering out the dicrotic notch, incisures, and/or false positives caused by a subject's respiration. For example, the pulse detection and characterization account for false positives by setting a minimum threshold range between the maximum and minimum bulk absorption points.

In one embodiment, the narrow-spectrum light source and the broad-spectrum light source can each be used to determine the minimum and maximum bulk absorption points. The minimum and maximum bulk absorption points of the narrow-spectrum light source and the minimum and maximum bulk absorption points of the broad-spectrum light source may be compared to determine the accuracy of the measurements or to calibrate the measurements taken using the narrow-spectrum and broad-spectrum light sources. In one example, a narrow-spectrum light source and a broad-spectrum light source are each used to determine the pulse oximetry information of a subject and the pulse oximetry information from the each light source is compared to the other to calibrate the measurements taken by one or both sources. In another example the pulse oximetry information from each light source can be compared to each other to determine the accuracy of the measurements taken by one or both sources. In another example the pulse oximetry information from each light source can be compared to a defined or reference data set to determine the accuracy of the measurements or to calibrate the measurements.

In one embodiment, at the maximum and minimum volumes, a broad-spectrum light source may be triggered to emit light in a broad spectrum. A broad-spectrum light detector may measure bulk absorption by the subject of the light in the broad spectrum. In another embodiment, a broad-spectrum light source may be used to determine the maximum and minimum volumes. When a maximum and/or minimum volume is detected, a measurement of bulk absorption by the subject of the light in the broad spectrum can be triggered. In another embodiment, a broad-spectrum light source may continuously measure the bulk absorption by the subject of the light in the broad spectrum. The broad-spectrum light source may be configured to emit light in at least a portion of the infrared (IR), visible, and/or ultraviolet (UV) spectrums.

In one embodiment, the maximum blood volume and minimum blood volume are used to filter out certain constituents or components of the appendage, such as a finger. In one example, the emitted light from the LED or broad-spectrum light source are absorbed and/or reflected by number of components of the finger including the tissue, bone, water, and blood. The amount of light absorbed and/or reflected by components of the finger such as the tissue, bone, and water are substantially constant or static over a short period of time, such as a few milliseconds, or change at a gradual rate. The bulk absorption measurement of these components may remain substantially constant, static, or gradually change because the amount or volume of tissue, bone, and/or water remains substantially constant, static, or gradually change over a short period of time. In contrast, the volume or amount of blood in the finger may change rapidly due to the pumping of blood through the circulatory system of an individual, as previously discussed. For example, as the heart contracts the blood volume in the finger of an individual increases to a maximum volume point and when the heart relaxes the blood volume decreases to a minimum volume point in the finger.

In one embodiment, a modified Beer's law can be used to account for the bulk absorption of light. The modified Beer's law can provide that light can be scattered in any or all directions. Because light is scattered in any given direction, the distance between an energy source and a target location are measured. The linear separation or difference in distance between an energy source and a target location are used to calculate a concentration of energy at the source and the concentration of energy at the target location to determine the difference in the concentration of energy.

In one embodiment, the modified Beer's law may be expressed as:

$$(i) = \frac{1}{d^2} i o e^{-\alpha(t)d} \text{ and } \alpha(t) = \frac{\log\left[\frac{(i)d^2}{-io}\right]}{-d},$$

where $\alpha(t) = \sqrt{3k(t)[k(t)+s(t)]}$, and it is assumed that $k(t) \ll s(t)$. Based on that assumption then $\alpha(t) = \sqrt{3k(t)s(t)}$. Noting that $k(t) = Xb(t)kb + Xo(t)Ko$ and $s(t) = Xb(t)sb + Xo(t)so$ and additionally that, $$Xb = \frac{Vb}{Vb + Vo} => Xb(t) = \frac{Vb(t)}{Vb(t) + Vo} \text{ and } Xo(t) = \frac{Vo}{Vb(t) + Vo}$$

where $\alpha$ is the bulk absorption; $\alpha(\ )$ is a bulk absorption as a function of a defined parameter; k is absorption; k( ) is absorption as a function of a defined parameter; s is scattering; s( ) is scattering as a function of a defined parameter; d is the distance of separation between a source and an detector; t is time; I is the measured intensity; io is the initial illumination; kb is the absorption of blood; ko is the absorption of all non-blood components; Xb is the volume percentage of blood; Xb is the volume percentage of blood; Xo is the volume of all non-blood components; sb is the scattering of blood components; so is a scattering of non-blood components; Xb1 is time at a first point, such as time at minimum blood volume; Xb2 is time at a second point, such as time at a maximum blood volume; αm is measured bulk absorption; and a.u. represents arbitrary units. In one embodiment, these equations and assumptions apply to scattering (s) components of the light in optical measurements of the subject.

Additionally, the proration of blood (Xb) can be further considered at two different states. For example at the minimum and maximum profusion in the finger during a power stroke cycle:

$$Xb1 = \frac{Vb1}{Vb1 + Vo}, Xo1 = \frac{Vo}{Vb1 + Vo}; \quad (6)$$

and $$Xb2 = \frac{Vb2}{Vb2 + Vo}, Xo2 = \frac{Vo}{Vb2 + Vo}. \quad (7)$$

It can be noted that:

$$\Delta Vb = \frac{Vb2 - Vb1}{Vbave + Vo} \sim .3\%$$

(8) and $$Vb2 = Vb1 \Delta Vb \quad (9).$$

Taking the $1^{st}$ differential:

$$Xb'(t) \sim \frac{\Delta Vb}{\Delta t} => Xb' \sim \Delta Vb \text{ for } \Delta t = 1 \ a.u.; \quad (10)$$

then $$Xb' = \frac{-Vb1}{Vb1 + Vo} + \frac{Vb1}{Vb1 + \Delta Vb + Vo} + \frac{\Delta Vb}{Vb1 + \Delta Vb + Vo}. \quad (11)$$

Noting that: $Vb1 + Vo \gg \Delta Vb$, it is assumed that: $Vb1 + \Delta Vb + Vo \sim Vb1 + Vo$. Therefore, $$Xb' \sim \frac{\Delta Vb}{Vb1 + Vo} \text{ and } Xo' \sim \frac{Vo}{Vb1 + \Delta Vb + Vo} - \frac{Vo}{Vb1 + Vo}.$$

Based on these assumptions, $$Xo' \sim \frac{Vo}{Vb1 + Vo} - \frac{Vo}{Vb1 + Vo} = 0$$

Therefore, it can be assumed that $Xo \sim$ constant.

Based on these equations and assumptions above, then taking $$\alpha(t) = \frac{\log\left[\frac{(i)d^2}{-io}\right]}{-d}$$

and taking the differential $$\alpha'(t) = -\frac{1}{d}\frac{i'(t)}{i(t)},$$

also $d\sqrt{3k(t)s(t)}=(\sqrt{3}(s(t)k'(t)+k(t)s'(t)))/2\sqrt{k(t)s(t)})$, and additionally defining $$\alpha m(t) = \frac{\text{Log}\left[\frac{(d)d^2}{-io}\right]}{3}k(t)s(t)$$

then $\alpha m'(t)=k'(t)s(t)+k(t)s'(t)$. Taking the second derivative and substituting:

$$\alpha m''(t) = 2\left(\frac{\Delta VbVb}{(Vb+Vo)^2}\right)' Kb\,Sb$$

and considering $$2\left(\frac{\Delta VbVb}{(Vb+Vo)^2}\right)' = f(Vb(t))$$

then the modified Beer's law can be solved as $$Kb\,Sb = \frac{\alpha m''}{f(Vb(t))}.$$

In turn, the quantity Kb*Sb contains the blood constituent information from which, using a multivariate analysis, the breakdown of blood in an in-vivo sample can be determined. Kb*Sb are the superposition absorption and scattering coefficients for blood. They are comprised of all effects of all of constituents of the blood sample which include all of the proteins, sugars, fats, water, foreign substances (e.g. drugs), etc. Generally it is not necessary that all quantities be determined. Rather, only target constituents may be determined. For example, hemoglobin may be determined in the case of anemia, or while blood cells in the case of infection, or glucose in the case of diabetes may be determined. The individual influence of each of these constituents on the superimposed bulk response is generally very subtle and therefore it some form of statistical base analysis can be employed. For instance, a multivariate analysis may be used to extract the individual constituent information. Various forms of multivariate analysis may be employed to process the bulk absorption data, including for example, least squares fitting techniques. In each case a calibration data set can be taken upon a representative population. The calibration data set can be processed via multivariate analysis to determine a calibration vector for the blood constituents across this population. This "b" or calibration vector can then be used in the operational measures to determine the results from an unknown data set for a given individual, thus providing the results desired.

In one embodiment, where the components of the appendage such as the tissue, bone, and water remain constant, static, or gradually change and the blood volume changes rapidly, a discrete bulk absorption measurement may be taken of the maximum and minimum volume point of the blood. A differential may be taken of the bulk absorption measurements at the maximum and minimum volume point in order to filter out the bulk absorption of components of the finger that remain constant or static over a period of time, such as tissue, water, and bone. In another example, after the bulk absorption measurements of components of an appendage such as the finger that remain constant or static over a period of time are filtered out, the bulk absorption measurement is comprised substantially of components that do change over time, such as the blood constituents.

In another embodiment, continuous bulk absorption measurements or repetitive bulk absorption measurements can be taken. A differential of the measurements can be performed to filter out the components of an appendage that remain substantially constant or static over a period of time. Alternatively, the continuous bulk absorption measurements or sequential bulk absorption measurements may be used to determine the minimum and maximum blood volume points in an appendage and a differential can be taken of the measurements to filter out the components of an appendage that remain substantially constant or static over a period of time, such as the time between the minimum and maximum blood volume points.

In one embodiment, the processor may determine the difference between the minimum blood volume and maximum blood volume. When the difference between the minimum blood volume and maximum blood volume is below a defined or selected threshold there may be insufficient data regarding the blood constituents. In one embodiment, if the volume change threshold is not met, then the user may need to increase the difference between the minimum blood volume and maximum blood volume. In one example, the user may warm the appendage to increase blood flow to the appendage which would increase the difference between the minimum blood volume and maximum blood volume. In another example, the user may perform cardiovascular exercises to increase blood flow to the appendage which would increase the difference between the minimum blood volume and maximum blood volume. In one embodiment, if the difference or separation between the minimum blood volume and maximum blood volume does not meet or surpass a threshold value then the bulk absorption data is insufficient and the amount of each constituent may not be determined.

The broad-spectrum light source may emit light long enough to have sufficient resolution to accurately identify constituents of the blood but short enough to prevent the blood volume from changing significantly during the measurement. For example, the broad-spectrum light source may emit light for a full cardiac period, e.g. from the minimum volume point to the maximum volume point or the maximum volume point to the minimum volume point to accurately identify the constituents. In one example the broad-spectrum light source can stop emitting light after it reaches the end of the cardiac period, e.g. after the maximum volume point or the minimum point has been reached. In one embodiment, the heart contraction stroke, also known as the power stroke, generally lasts for a period of approximately 100 to 110 milliseconds. In another example, the broad-spectrum light source will continuously emit light throughout multiple cardiac periods and the spectrometer or processor can be configured to distinguish the bulk absorption measurements taken during each cardiac period.

A typical period of an inflection point at which the volume of blood is at a maximum or minimum is approximately 20-30 milliseconds. In one embodiment, the broad-spectrum light source may emit light for the approximately 20-30 milliseconds to allow a measurement to be taken over this period. In one embodiment, the broad-spectrum light detector may measure bulk absorption for only the desired time period, and/or unnecessary measurements may be discarded.

A fast Fourier transform (FFT) may be used to convert measurements from the time domain to the frequency domain (e.g., to calculate spectral characteristics). Various alternative frequency transforms may be used instead of or in addition to the FFT to calculate spectral characteristics, such as a discrete wavelet transform (DWT), a discrete cosine transform (DCT), a Laplace/Z-Transform, or the like. A processor may calculate the spectral characteristics of measurements received from the broad-spectrum light detector using a frequency transform. Each set of bulk absorption measurements for a maximum or minimum blood volume may be independently transformed. Frequency transforms of bulk absorption measurements for several maximum (or minimum) blood volumes may be averaged to remove dynamic noise and further improve the SNR of the measurements.

A time-varying component of the bulk absorption measurements may be extracted by performing a mathematical comparison operation between a frequency transform of the bulk absorption measurements at the maximum blood volume and a frequency transform of the bulk absorption measurements at the minimum blood volume. Various comparison operations may be used, such as subtraction, division, ratio, a derivative, or the like. For example, a difference or ratio between bulk absorption at the maximum blood volume and bulk absorption at the minimum blood volume may correspond in a determinable way with the bulk absorption spectrum of the constituents of the blood. The difference may comprise a plurality of points computed from a point-by-point comparison of the frequency-transformed bulk absorption measurements at the maximum blood volume to the frequency-transformed bulk absorption measurements at the minimum blood volume.

Multivariate analysis may be performed on the time-varying component of the bulk absorption measurements to determine the amount of each constituent of the blood. In one embodiment, spectroscopy may be used to take constituent measurements while concurrent measurements are taken using other devices or equipment to measure oxygen levels, protein levels, etc. The information collected using multiple devices or methods may then be correlated and/or aggregated or combined and analyzed using multivariate analysis, such as a least squared means, to determine the proper coefficients that enable curve fitting of the raw or initial spectroscopy data to a predetermined curve. The predetermined curve may be determined based on other types of measurements of similar blood constituents or body components, such as invasive measurements. Alternatively, the predetermined curve may be a composite average taken over a selected sample of subjects, such as 25, 50, 100 or more subjects.

The bulk absorption measurements may be calibrated or adjusted to account for interference or noise that may occur during the measurement. There are multiple variables that may cause interference or noise in the bulk absorption measurement data of a subject, such as the amount of tissue, bone, water, and blood in an appendage, other constituents and/or non-blood constituents absorbing or reflecting light or energy, subject respiration, movement of the body or appendage, light or energy from other sources, electrical noise in the emitters and/or detectors, and so forth. In one embodiment, the bulk absorption measurements may be calibrated or adjusted using a curve fitting function. For instance, the curve fitting can be based on interpolation. In another embodiment the curve fitting function can use a smoothing function. In one embodiment, to account for the multiple variables and calibrate the bulk absorption measurements, the bulk absorption measurements of a subject are compared to the bulk absorption measurement data of a reference data set. In another embodiment, bulk absorption measurement data can be collected on multiple other subjects and the calibration can be based on comparing the bulk absorption measurement data of the subject to the bulk absorption measurement data of the multiple subjects.

In one embodiment, the calibration information may be used to determine a calibration curve. The bulk absorption data of the subject can be curved fitted to the predetermined calibration curve. In another embodiment, the calibration information can be used to determine a calibration vector. For example, the bulk absorption data of the subject can be calibrated based on performing a dot product using a calibration vector and the bulk absorption data of the subject. In another embodiment, the bulk absorption measurements of the subject may be calibrated using a multivariate analysis. In one example, the multivariate analysis may include multiple parameters or variables of the individual such as an oxygen level, protein level, etc. in calibrating the bulk absorption measurement data. In another example, the multivariate analysis may use multiple parameters or an aggregate of the bulk absorption measurement information from other or multiple subjects.

In an embodiment, the noninvasive blood monitoring platform can provide the bulk absorption measurement(s) from which biometrical medical and biometrical identification parameters can be derived. The medical parameters and identification parameters may be derived by performing computations on a single (composite) set of bulk absorption measurements. The medical parameters and identification parameters may be unique or specific for a given individual. Alternatively, a plurality of identification parameters may be substantially unique in the aggregate. The medical parameters may be measurements of a medical status of the subject. The security parameters may be used to identify the subject. The security parameters may be used to provide privacy and/or restrict access to medical information of a subject. The security parameters may be used to ensure compliance with the Health Insurance Portability and Accountability Act (HIPAA). In an embodiment, the security parameters may be used when storing medical parameters to associate the medical parameters with the subject and restrict access to the stored medical parameters.

In another embodiment, the noninvasive blood monitoring platform may be used to provide a plurality of identification parameters or information related to the subject. For example, the identification parameters can include skin color, depth and shape of the dicrotic notch, O2 saturation, blood pressure, heart rate, blood constituent levels, or other desired parameters. The plurality of identification parameters, in aggregate, can be used to create a substantially unique identification profile. The unique identification profile or information of the subject may be used to identify the person. For example, the noninvasive blood monitoring platform may identify an individual for automatic data acquisition tagging based on selected unique identification parameters or information of the individual. One advantage of using the unique identification profile or information for automatic data acquisition tagging may be that the time necessary to accurately identify the person is shortened. Another advantage is the identifying nature of the measurement is self-contained. That is, the data set itself can be used to identify the source of the data. This significantly reduces the probability of losing the data or misidentifying the subject with which the data is associated.

For example, the noninvasive blood monitoring platform may be used by a group of people, such as a family or multiple people at a medical facility. In order to identify each person, a pass code or personal identification number (PIN) may typically be used. Instead of requiring a pass code, the identification parameters can be used to identify each person based on the analysis of their bulk absorption measurement or the raw data provided in their bulk absorption measurement. In one embodiment, the medical and biometrical identification parameters may be used in combination to provide for automation of identification and the performing of medical measurements. For example, a person at home or at a medical facility may use a noninvasive blood monitoring platform to take a medical measurement or determine a medical parameter. At substantially the same instance as the medical measurement is taken, the person can be identified using the identification parameters and/or the medical measurement can be associated with the person. Several advantages of the automation of taking identification and medical parameters at substantially the same instance can include the elimination of requiring a separate identification step, increasing efficiency, increasing medical data security, and providing a self-contained identification and medical measurement platform. The automation of identification and association of the medical parameters with a subject can also provide additional benefits while using the platform in the field. For instance, when using the platform in third world countries, ability to identify people based on selected identification parameters can reduce the amount of paperwork and increase the security and reliability of measurements made.

Another advantage of using the unique identification parameters or information for automatic data acquisition tagging may be a reduction in complexity of identifying the person non-invasively while maintain a sufficient level of accuracy and/or security. The unique identification profile may be used as a component of patient security.

FIG. 1 is a schematic diagram of a platform 100 for noninvasive blood measurement. The platform 100 may be configured to attach to a finger 180 of a subject. For example, a housing (not shown), such as a polymer clip, may couple the platform 100 to the finger 180. When the platform 100 is coupled to the finger 180, a plurality of light sources 112, 120 may be configured to emit light at the finger 180, and a plurality of detectors 114, 130 may be configured to measure bulk absorption by the finger 180 of the emitted light.

A light-emitting diode (LED) 112 may be configured to emit light in a narrow spectrum, such as at a discrete wavelength. In alternate embodiments, a laser, laser diode, phosphor, and/or the like may be used as a narrow spectrum light source in addition to or instead of the LED 112. For example, the LED 112 may be configured to emit light in the IR, visible, and/or UV, spectrums. For example, in an embodiment, the LED 112 may be configured to emit light at 805 nanometers (nm). A photodiode 114 may be configured to measure the intensity of received light in a predetermined spectrum. For example, the photodiode 114 may include an optical filter configured to block light not coming from the LED 112.

The LED 112 and/or the photodiode 114 may be communicatively coupled to a processing unit 115. The processing unit 115 may include analog and/or digital circuitry, such as a special-purpose processor, and the circuitry may be contained on a single circuit board. The processing unit 115 may include, for example, a control circuit to drive the LED 112. The processing unit 115 may receive measurements from the photodiode 114. The processing unit 115 may perform analog processing on the measurements and/or convert the measurements from analog to digital and perform digital processing on the measurements to detect blood volume maximums and/or blood volume minimums. In another embodiment, indicators such as blood oxygen levels or pulse may be used in detecting blood volume maximums and/or blood volume minimums. As previously discussed, when a blood volume maximum or a blood volume minimum is detected, the processing unit may send a trigger signal to a broad-spectrum light source 120 and/or a spectrometer 130.

In response to the trigger signal, the broad-spectrum light source 120 may emit broad-spectrum light. The broad-spectrum light source 120 may emit light that occupies at least a portion of a plurality of spectrums, such as the IR, visible, and/or UV spectrums, for a predetermined time period. For example, the broad-spectrum light source may emit light for 20-30 milliseconds in an embodiment. Similarly, the spectrometer 130 may detect light for a predetermined time period, which may be less than and/or encompassed by the predetermined time period during which light is emitted. For example, the spectrometer 130 may detect light for less than 10-15 milliseconds. In one embodiment, the period of 10-30 milliseconds is the approximate period where a minimum or maximum volume point remains static or relatively fixed. An emission spectrum of the broad-spectrum light source 120 may encompass and/or overlap with an emission spectrum of the spectrometer 130.

The spectrometer 130 may be configured to measure bulk absorption by the finger 180 of the broad-spectrum light. The spectrometer 130 may measure bulk absorption by comparing an intensity of light received by the spectrometer 130 and comparing the received intensity to emission intensity. The spectrometer 130 may be configured to determine the bulk absorption as a function of frequency. For example, the spectrometer 130 may use a frequency transform to convert bulk absorption measurements captured at a plurality of time values to bulk absorption measurements expressed as a function of frequency and/or wave length. Alternatively, or in addition, a computer 140 may calculate a frequency transform of the bulk absorption measurements. In various embodiments, the spectrometer 130 may instead be a semiconductor sensor (e.g., a photodiode, photovoltaic sensor, or the like). The spectrometer 130 may include a broad-spectrum bandpass filter that passes only frequencies of interest.

The spectrometer 130 may be communicatively coupled to a computer 140. The computer 140 may receive the bulk absorption measurements made by the spectrometer 130 including bulk absorption measurements at a maximum blood volume and bulk absorption measurements at a minimum blood volume. The bulk absorption measurements may be frequency transformed or may be expressed as a function of time. The computer 140 may perform a frequency transform on the bulk absorption measurements if one has not already been done. A time-varying component of the frequency-transformed bulk absorption measurements may be extracted by the computer 140 by performing a mathematical comparison operation between the bulk absorption measurements at the maximum blood volume and the bulk absorption measurements at the minimum blood volume. The computer 140 may determine the amount(s) (e.g., concentration) of one or more constituents of the blood by performing multivariate analysis on the time-varying component extracted by the computer 140. The computer 140 may include an output device for indicating the amount(s) of the one or more constituents and/or may save the determined amount(s).

Figure 2:
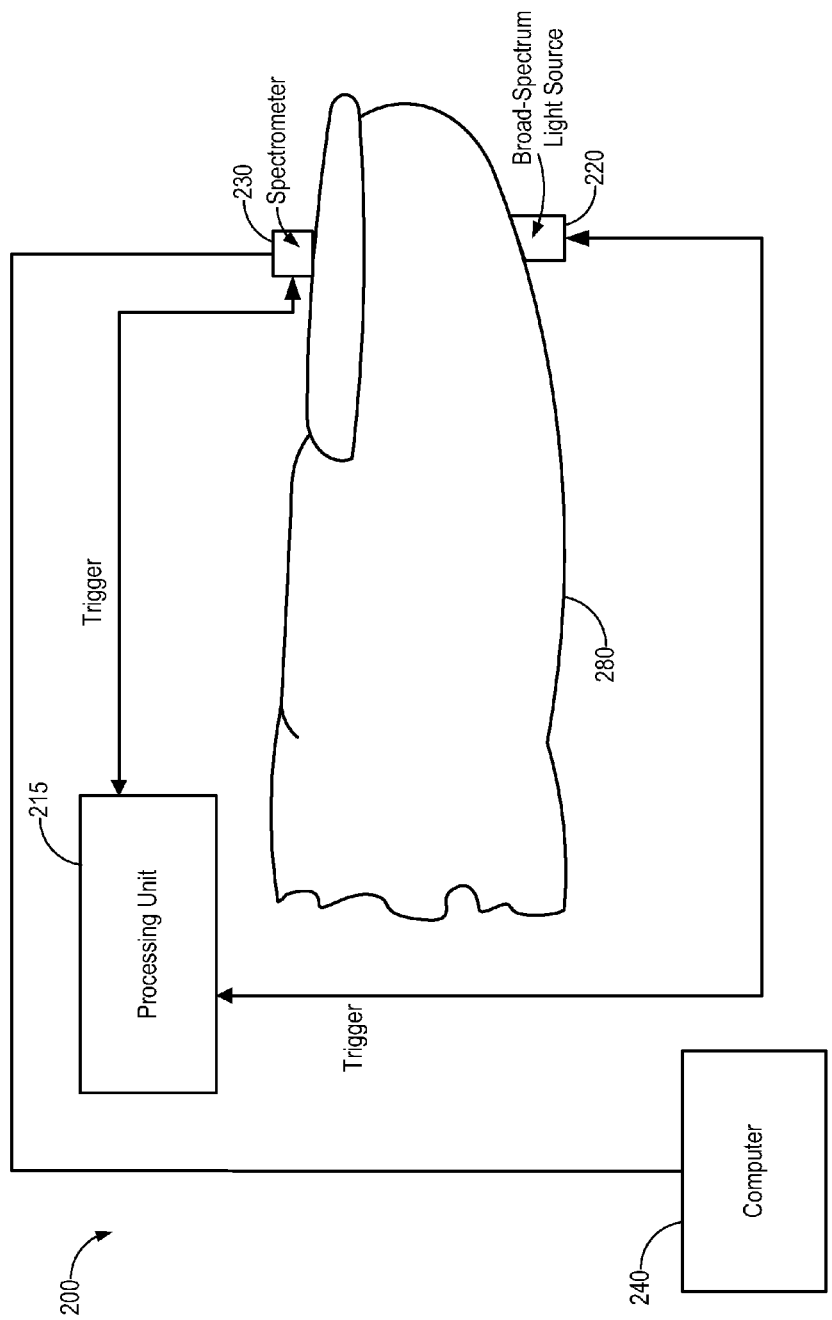
FIG. 2 is a schematic diagram of an apparatus for noninvasive blood measurement in accordance with an example.

FIG. 2 is a schematic diagram of a platform 200 for noninvasive blood measurement. The platform 200 may be configured to attach to a finger 280 of a subject. For example, a housing (not shown), such as a polymer clip, may couple the platform 200 to the finger 280. When the platform 200 is coupled to the finger 280, a broad-spectrum light source 220 may be configured to emit light at the finger 280, and a detector 230, such as a spectrometer may be configured to measure bulk absorption by the finger 280 of the emitted light. In contrast with the example of FIG. 1, only the broad spectrum light source 220 and spectrometer 230 are present in the platform in the example of FIG. 2.

The broad-spectrum light source 220 may be configured to emit light at a selected light spectrum range, such as approximately 400 nm to 1150 nm. In another embodiment, the broad-spectrum light source 220 may emit light that occupies at least a portion of a plurality of spectrums, such as the IR, visible, and/or UV spectrums. The spectrometer 230 may be configured to measure the intensity of received light at the selected light spectrum range. The broad-spectrum light source 220 and/or the spectrometer 230 may be communicatively coupled to a processing unit 215. The processing unit 215 may include analog and/or digital circuitry, such as a special-purpose processor or a computer processor, and the circuitry may be contained on a single circuit board or multiple circuit boards. The processing unit 215 may include, for example, a computer readable medium and a control circuit to drive the broad-spectrum light source 220. The processing unit 215 may receive measurements from the spectrometer 230. The processing unit 215 may perform analog processing on the measurements and/or convert the measurements from an analog form to a digital form and perform digital processing on the measurements to detect blood volume maximums and/or blood volume minimums, as previously discussed. In one embodiment, the broad-spectrum light source 220 can continuously emit light. In another embodiment, when a blood volume maximum or a blood volume minimum is detected, the processing unit 215 may send a trigger signal to the broad-spectrum light source 220 and/or a spectrometer 230. The trigger signal sent to the broad-spectrum light source 220 may last longer than and encompass the trigger signal to the spectrometer 230.

In response to the trigger signal, the broad-spectrum light source 220 may emit broad-spectrum light. The broad-spectrum light source 220 may emit light for a predetermined time period. For example, the broad-spectrum light source may emit light for 20-30 milliseconds in one example embodiment. Similarly, the spectrometer 230 may detect light for a predetermined time period, which may be less than and/or encompassed by the predetermined time period during which light is emitted. For example, the spectrometer 230 may detect light for approximately 10-15 milliseconds. An emission spectrum of the broad-spectrum light source 220 may encompass and/or overlap with a detection spectrum of the spectrometer 230.

The spectrometer 230 may be configured to measure bulk absorption by the finger 280 of the broad-spectrum light. The spectrometer 230 may measure bulk absorption by measuring an intensity of light received by the spectrometer 230 and comparing the received intensity to an emission intensity. The spectrometer 230 may be configured to determine the bulk absorption as a function of frequency. For example, the spectrometer 230 may use a frequency transform to convert bulk absorption measurements captured at a plurality of time values to bulk absorption measurements expressed as a function of frequency and/or wave length. Alternatively, or in addition, a computer 240 or processing unit 215 may calculate a frequency transform of the bulk absorption measurements. In various embodiments, the spectrometer 230 may instead be a semiconductor sensor (e.g., a photodiode, photovoltaic sensor, or the like). The spectrometer 230 may include a broad-spectrum bandpass filter that passes only frequencies of interest.

The spectrometer 230 may be communicatively coupled to a computer 240. The computer 240 may receive the bulk absorption measurements made by the spectrometer 230 including bulk absorption measurements at a maximum blood volume and bulk absorption measurements at a minimum blood volume. The bulk absorption measurements may be frequency transformed or may be expressed as a function of time. The computer 240 may perform a frequency transform on the bulk absorption measurements if one has not already been done. A time-varying component of the frequency-transformed bulk absorption measurements may be extracted by the computer 240 by performing a mathematical comparison operation between the bulk absorption measurements at the maximum blood volume and the bulk absorption measurements at the minimum blood volume. The computer 240 can be configured to determine the amount(s) (e.g., concentration) of one or more constituents of the blood by performing a multivariate analysis on the time-varying component extracted by the computer 240. The computer 240 may include an output device for indicating the amount(s) of the one or more constituents and/or may save the determined amount(s).

Figure 3:
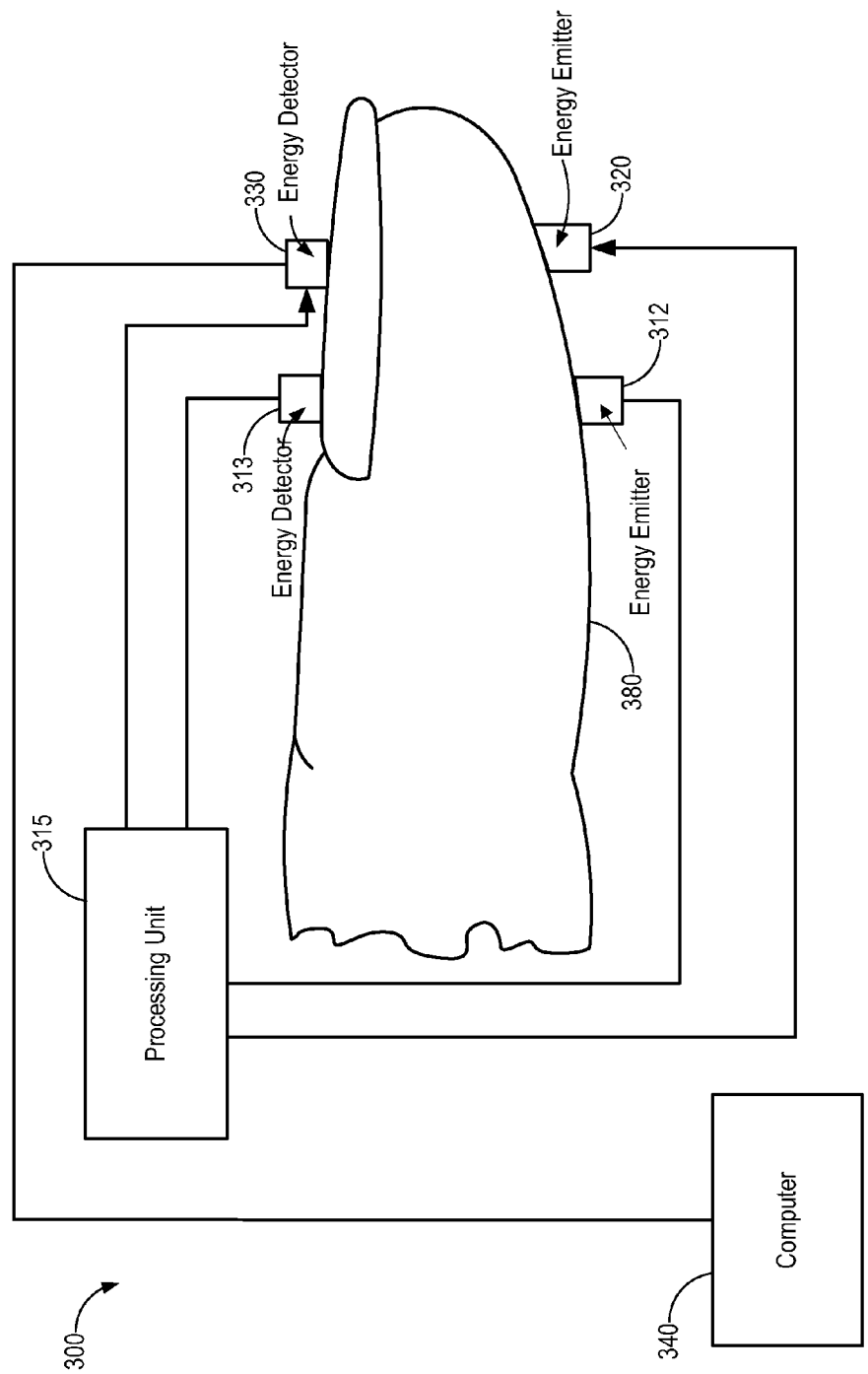
FIG. 3 is a schematic diagram of an apparatus for noninvasive blood measurement in accordance with an example.

FIG. 3 is a schematic diagram of a platform 300 for noninvasive blood measurement. The platform 300 may be configured to attach to a finger 380 of a subject. For example, a housing (not shown), such as a polymer clip, may couple the platform 300 to the finger 380. When the platform 300 is coupled to the finger 380, a plurality of energy emitters 312, 320 may be configured to emit energy at the finger 380, and a plurality of energy detectors 314, 330 can be configured to measure bulk absorption by the finger 180 of the emitted energies.

In one example, one or both of the energy emitters 312, 320 may be configured to emit an electrical signal. The energy detector(s) 314, 330 can be configured to measure an intensity of a received electrical signal transmitted through a portion of a subject, such as a finger in this example. In one embodiment, the electrical signal can be a radio frequency signal with a frequency ranging from 1 kilohertz to 100 Megahertz. In one embodiment, the energy detector(s) 314, 330 may be an impedance spectrometer.

In another example, the energy emitters 312, 320 may be configured to emit an optical or acoustic signal. The energy detector(s) 314, 330 can be configured to measure an intensity of a received acoustic or optical signal transmitted through a portion of a subject, such as a finger in this example. As previously discussed, the optical emitter may be a narrow band or broad band optical emitter.

The energy emitters 312, 320 can be used to emit signals that are mutually orthogonal to one another. The mutually orthogonal signals can be used to derive additional information than can be obtained from coherent signals.

The energy emitters 312 and/or 320 and/or the energy detectors 314 and/or 330 may be communicatively coupled to a processing unit 315. The processing unit 315 may include analog and/or digital circuitry, such as a special-purpose processor, and the circuitry may be contained on a single circuit board. The processing unit 315 may include, for example, a control circuit to drive the energy emitter(s) 312 and/or 320. The processing unit 315 may receive measurements from the energy detectors 314 and/or 330. The processing unit 315 may perform analog processing on the measurements and/or convert the measurements from analog to digital and perform digital processing on the measurements to detect blood volume maximums and/or blood volume minimums. In another embodiment, indicators such as blood oxygen levels or pulse may be used in detecting blood volume maximums and/or blood volume minimums. When a blood volume maximum or a blood volume minimum is detected, the processing unit may send a trigger signal to the energy emitters 312 and/or 320 and/or the energy detectors 314 and/or 330.

In response to the trigger signal, the energy sources 312 and/or 320 may emit energy, such as an electrical energy, acoustic energy, light energy, etc. For example, the energy sources 312 and/or 320 may emit energy for 20-30 milliseconds in an embodiment. Similarly, the energy detectors 314 and/or 330 may detect energy for a predetermined time period, which may be less than and/or encompassed by the predetermined time period during which light is emitted. For example, the energy detectors 314 and/or 330 may detect energy for less than 10-15 milliseconds. In one embodiment, the period of 10-15 milliseconds is the approximate period where a minimum or maximum volume point remains static or relatively fixed. An emission spectrum of the energy emitters 312 and/or 320 may encompass and/or overlap with an emission spectrum of the energy detectors 314 and/or 330.

The energy detectors 314 and/or 330 may be configured to measure bulk absorption by the finger 380 of the energy. The energy detectors 314 and/or 330 may measure bulk absorption by measuring an intensity of energy received by the energy detectors 314 and/or 330 and comparing the received intensity to an emission intensity. In another embodiment, the energy detectors 314 and/or 330 may take acoustic measurements, electrical signal measurements, light signal measurements, electromagnetic radiation measurements, thermal measurements, vibrational measurements, and/or time measurements. The energy detectors 314 and/or 330 may be configured to determine the bulk absorption as a function of frequency. For example, the energy detectors 314 and/or 330 may use a frequency transform to convert bulk absorption measurements captured at a plurality of time values to bulk absorption measurements expressed as a function of frequency and/or wave length. Alternatively, or in addition, a computer 340 may calculate a frequency transform of the bulk absorption measurements. In various embodiments, the energy detectors 314 and/or 330 may instead be a semiconductor sensor (e.g., a photodiode, photovoltaic sensor, or the like). The energy detectors 314 and/or 330 may include a bandpass filter that passes only defined or selected frequencies of interest.

The energy detectors 314 and/or 330 may be communicatively coupled to a computer 340. The computer 340 may receive the bulk absorption measurements made by the energy detectors 314 and/or 330 including bulk absorption measurements at a maximum blood volume and bulk absorption measurements at a minimum blood volume. The bulk absorption measurements may be frequency transformed or may be expressed as a function of time. The computer 340 may perform a frequency transform on the bulk absorption measurements if one has not already been done. A time-varying component of the frequency-transformed bulk absorption measurements may be extracted by the computer 340 by performing a mathematical comparison operation between the bulk absorption measurements at the maximum blood volume and the bulk absorption measurements at the minimum blood volume. The computer 340 can be configured to determine the amount(s) (e.g., concentration) of one or more constituents of the blood by performing multivariate analysis on the time-varying component extracted by the computer 340. The computer 340 may include an output device for indicating the amount(s) of the one or more constituents and/or may save the determined amount(s).

Figure 4:
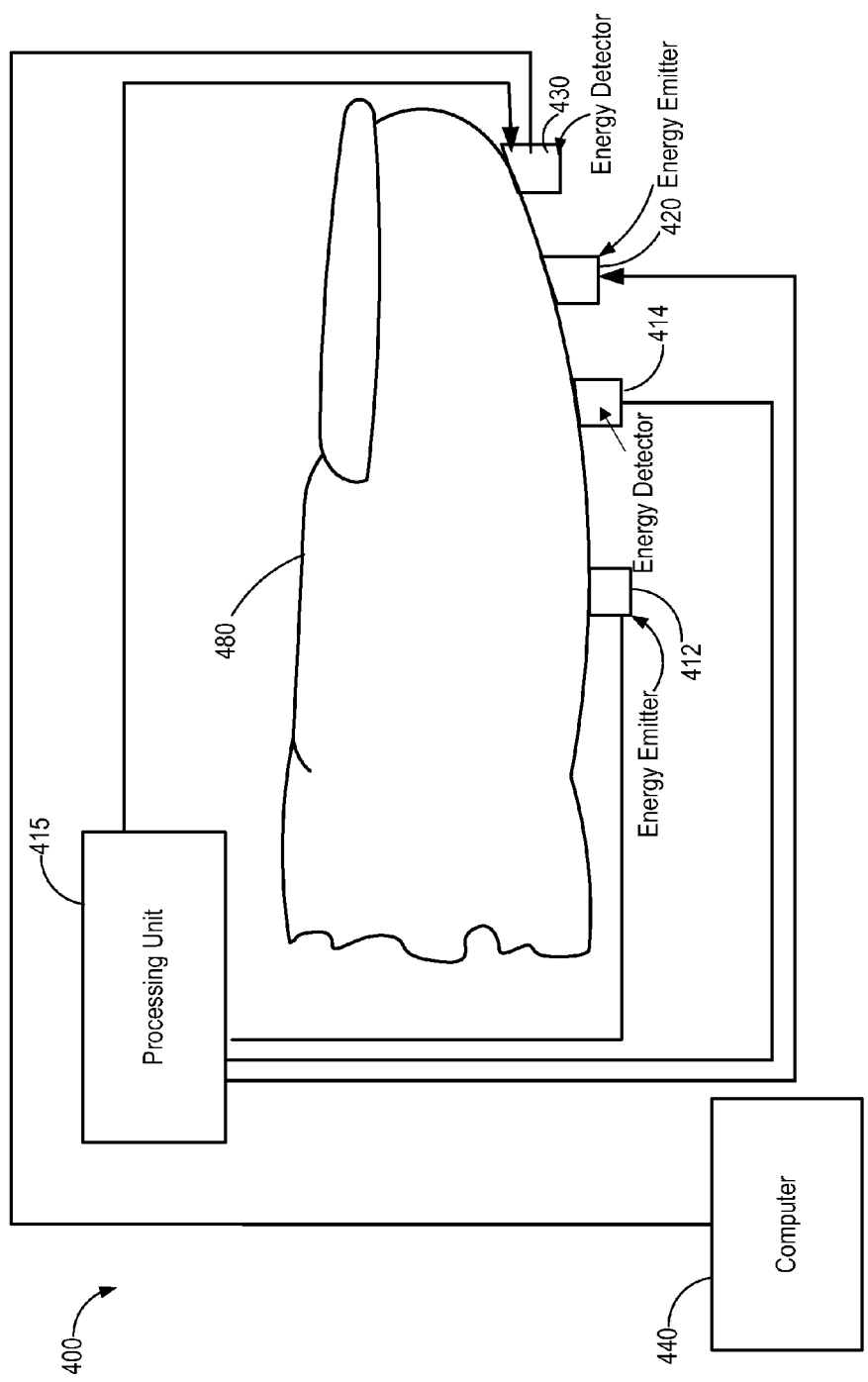
FIG. 4 is another schematic diagram of an apparatus for noninvasive blood measurement in accordance with an example.

While the examples illustrated in FIGS. 1-3 show the energy emitter on one side of a subject's appendage, such as a finger, and the energy detector on another side of the appendage, this is not intended to be limiting. FIG. 4 is a schematic diagram of another embodiment of a platform 400 for noninvasive blood measurement. The platform 400 may be configured to attach to a finger 480 of a subject. FIG. 4 illustrates that it can be preferable to have energy detectors 414 and 430 located on a same side of an appendage as an energy emitters 412 and 420, and located a selected distance from the energy emitters 412 and 420, respectively. For example, the energy detector 414 and energy emitter 412 may be placed 5 to 20 millimeters (mm) apart at a bottom of a finger, or other desired appendage. The actual separation can depend on the type of measurement being performed, the type of energy produced by the emitter, and the appendage at which a measurement is performed. Placing the energy detector and the energy emitter on a same side of an appendage can increase an amount of energy detected due to a potentially reduced distance between the emitter and detector, and the types of cellular structures that the energy travels through. For instance, by placing the energy emitter and energy detector on a same side of an appendage, the detected energy typically does not travel through a bone. The increased amount of energy at the detector can simplify detection and analysis of the received energy. The platform 400 for noninvasive blood measurement can perform substantially similar as previously described with respect to platform 300.

Figure 5:
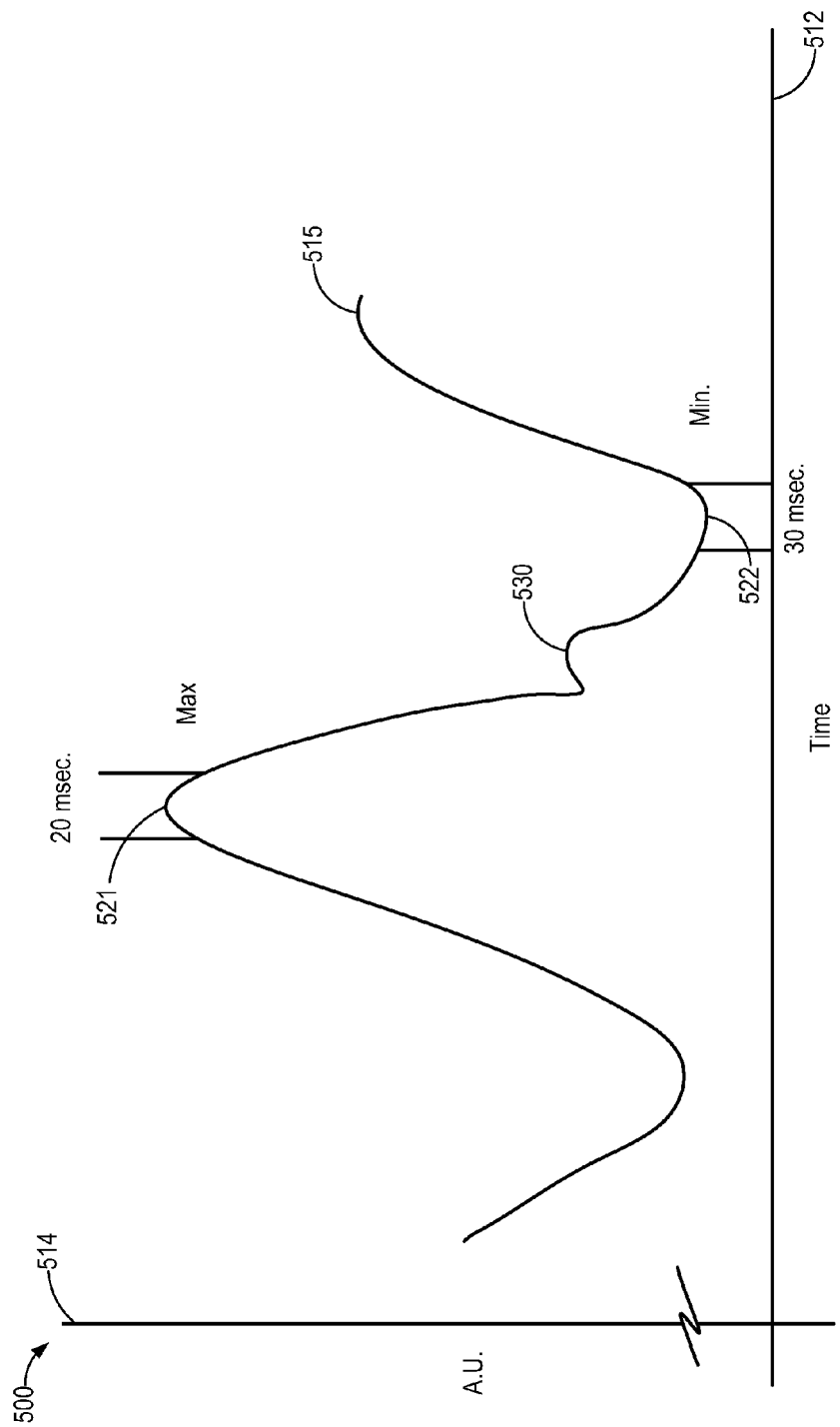
FIG. 5 is a graph of an exemplary photoplethysmograph detected by the photodiode in accordance with an example.

FIG. 5 is a graph 500 of an exemplary photoplethysmograph (PPG) 515 detected by the photodiode 114. The graph 500 includes time as an x-axis 512 and absorbance units (AU) as a y-axis 514. The processing unit 115 may be configured to detect a maximum blood volume 521 and a minimum blood volume 522 based on the PPG 515 and transmit a trigger signal to the broad-spectrum light source 120 and spectrometer 130. The dicrotic notch 530 may create false maximum and minimum points as there is a minor increase and decrease in arterial pulse. A processing unit, such as processing unit 115 in the example of FIG. 1, may filter out or calibrate the absorption measurement data to account for the dicrotic notch 530. In the illustrated embodiment, the processing unit 115 may transmit the trigger signal for approximately 20 milliseconds at the blood volume maximum 521 and for approximately 30 milliseconds at the blood volume minimum 522. Because the blood volume maximum 521 is a sharper peak than the blood volume minimum 522, the corresponding trigger signal may be shorter in time to avoid making broad-spectrum measurements when the blood volume is changing rapidly. The blood volume maximum 521 and minimum 522 may be detected based on a slope of the PPG 515 falling below a predetermined threshold and/or the PPG 515 exceeding or falling below predetermined maximum and minimum thresholds.

Figure 6:
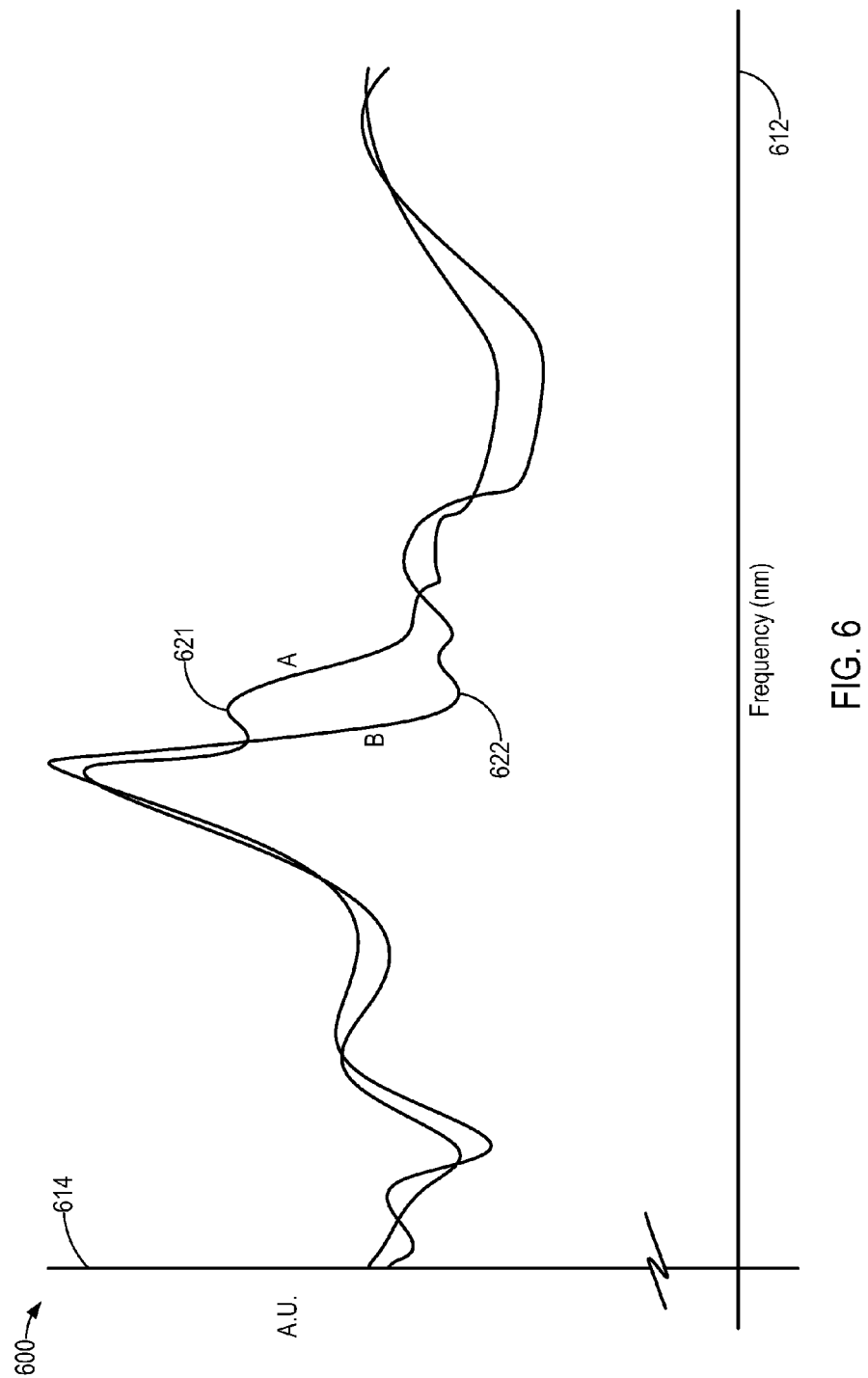
FIG. 6 is a graph of frequency-transformed bulk absorption measurements at the blood volume maximum and the blood volume minimum in accordance with an example.

FIG. 6 is a graph 600 of frequency-transformed bulk absorption measurements at the blood volume maximum 621 and the blood volume minimum 622. The graph 600 includes frequency expressed in nanometers as an x-axis 612. Because the wave length of light has a direct relationship with the frequency, the frequency may be expressed in nanometers. The scale for the y-axis 614 may be AU. The bulk absorption spectra 621, 622 may be different from one another due to the amount of blood absorbing light changing between the blood volume maximum and the blood volume minimum. Accordingly, the differences may be used to extract a time-varying component of the bulk absorption measurements that corresponds with the constituents of the blood. Multivariate analysis may be used on the time-varying component to determine the amount of the constituents.

Figure 7:
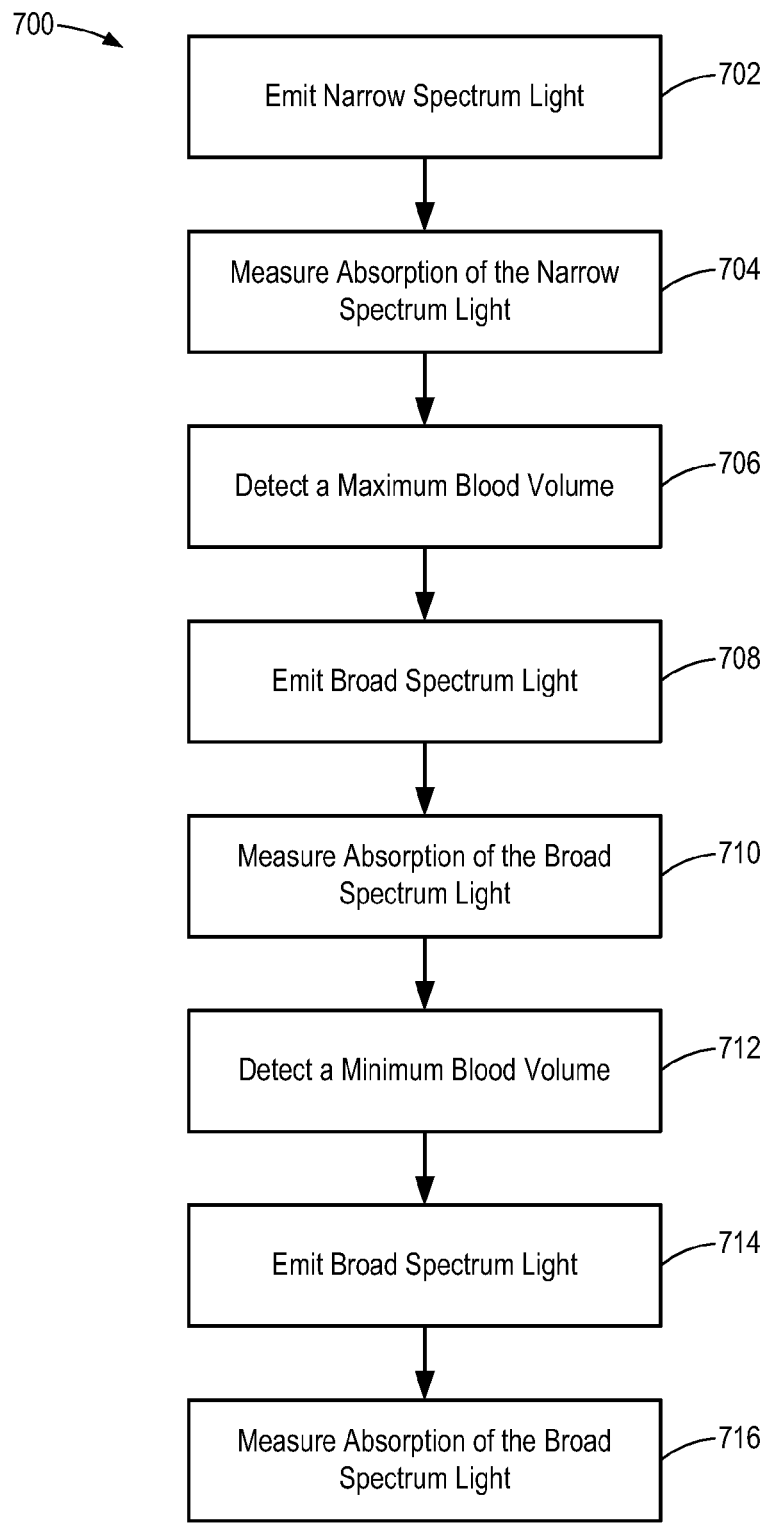
FIG. 7 is a flow diagram of a method 700 for acquiring bulk absorption measurements at the maximum and minimum blood volumes in accordance with an example.

FIG. 7 is a flow diagram of a method 700 for acquiring bulk absorption measurements at the maximum and minimum blood volumes. The LED 112 may emit 702 narrow-spectrum light continuously for a predetermined and/or indefinite period of time. The LED 112 may emit 702 narrow-spectrum light until amounts of each constituent are determined. Alternatively, or in addition, the LED 112 may continue to emit 702 light, and the noninvasive blood measurement platform 100 may continue to update the determined amounts of each constituent until a user input indicates to end measurement and/or until a predetermined time period has elapsed.

Referring to FIGS. 1 and 7, the photodiode 114 may measure 704 bulk absorption by the finger 118 of the narrow-spectrum light. In an embodiment, measuring 704 bulk absorption may include the photodiode 114 measuring intensity of received light and the processing unit 115 determining bulk absorption based on the received intensity and the emission intensity. Alternatively, the photodiode 114 may be configured to determine bulk absorption rather than the processing unit 115, and the photodiode 114 may communicate the determined bulk absorption to the processing unit 115.

Based on the bulk absorption measurements, the processing unit 115 may detect 706 a maximum blood volume. The bulk absorption may correspond directly with the blood volume, so the maximum blood volume may be detected 706 by determining when the maximum bulk absorption occurs. The maximum bulk absorption may be determined based on when the bulk absorption exceeds a predetermined threshold and/or when the rate of change of the bulk absorption is less than a predetermined threshold (e.g., a first derivative of the bulk absorption is less than predetermined threshold.)

The processing unit 115 may transmit a trigger signal to the broad-spectrum light source 120 and/or the spectrometer 130 while the maximum bulk absorption is detected. For example, the trigger signal may be transmitted as long as the bulk absorption exceeds a predetermined threshold and/or as long as the rate of change of the bulk absorption is less than a predetermined threshold. Alternatively, the trigger signal may be transmitted for a predetermined time period. The trigger signal may be configured to straddle the maximum, so the processing unit 115 may be configured to start transmission slightly before the maximum and end transmission slightly after the maximum. The trigger signal to the spectrometer 130 may begin transmission after the trigger signal to the broad-spectrum light source 120 once a predetermined time delay has passed. Similarly, the trigger signal to the spectrometer 130 may end a predetermined time period before the trigger signal to the broad-spectrum light source 120. The offset start and end times may ensure that the spectrometer 130 only measures bulk absorption while the broad-spectrum light source 120 is emitting light.

In response to the trigger signal, the broad-spectrum light source 120 may emit 508 broad-spectrum light at the finger 180. The broad-spectrum light source 120 may emit light occupying at least a portion of one or more spectrums, such as the IR spectrum, the visible spectrum, and/or the UV spectrum. The emission spectrum of the broad-spectrum light source 120 may be selected based on the particular constituents of the blood to be detected.

The broad-spectrum light source 120 may be configured to emit 714 broad-spectrum light at the finger 180. The spectrometer 130 may measure 716 bulk absorption by the finger 180 of the broad-spectrum light. The spectrometer 130 and/or the computer 140 may determine the bulk absorption by measuring the intensity of received light and comparing it to the intensity of emitted light. Steps 706-716 may occur once or a plurality of iterations may be repeated so multiple measurements can be averaged to improve accuracy and/or precision.

The spectrometer 130 may measure 710 bulk absorption by the finger of the broad-spectrum light emitted by the broad-spectrum light source 120. The spectrometer 130 may include a light intensity measuring device configured to measure the intensity of received light at any wavelength. Additionally, the spectrometer 130 may include a filter configured to have a passband corresponding to the emission spectrum of the broad-spectrum light source 120. The spectrometer 130 and/or the computer 140 may determine the bulk absorption from the emission intensity of the broad-spectrum light and the measured intensity of the received light. The spectrometer 130 and/or the computer 140 may at least temporarily store the bulk absorption measurements at the maximum blood volume.

The LED 112 and the photodiode 114 may continue to emit 702 and measure 704 bulk absorption of the narrow-spectrum light. The processing unit 115 may then detect 712 a minimum blood volume. Similar to detecting 706 the maximum blood volume, the processing unit 115 may detect 712 the minimum blood volume by determining when the bulk absorption measurement reaches a minimum value (e.g., the bulk absorption measurement and/or a rate of change of the bulk absorption measurement is below a predetermined threshold). The processing unit 115 may transmit a trigger signal to the broad-spectrum light source 120 and/or the spectrometer 130 as long as a minimum value is detected and/or for a predetermined time period.

Figure 8:
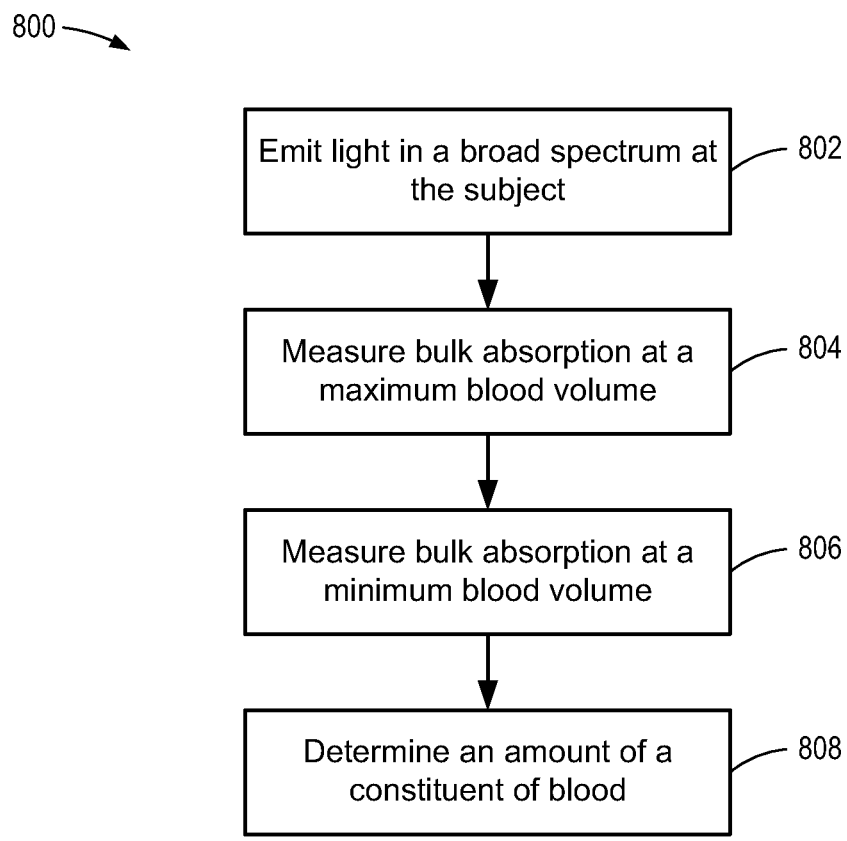
FIG. 8 is a flow chart to illustrate the functionality of one embodiment of the apparatus for noninvasive measurement of blood constituents in a subject in accordance with an example.

FIG. 8 uses a flow chart to illustrate the functionality of one embodiment of the apparatus for noninvasive measurement of blood constituents in a subject. The apparatus can comprise a broad-spectrum light source configured to emit light in a broad spectrum at the subject, as in block 802. The apparatus can further comprise a broad-spectrum light detector configured to measure bulk absorption by the subject of the light emitted by the broad-spectrum light source, wherein the broad-spectrum light detector is configured to measure bulk absorption at a maximum blood volume, as in block 804, and measure bulk absorption at a minimum blood volume, as in block 806. The apparatus can also comprise a processor configured to receive bulk absorption measurements from the broad-spectrum light detector and determine an amount of at least one constituent of the blood, as in block 806.

Figure 9:
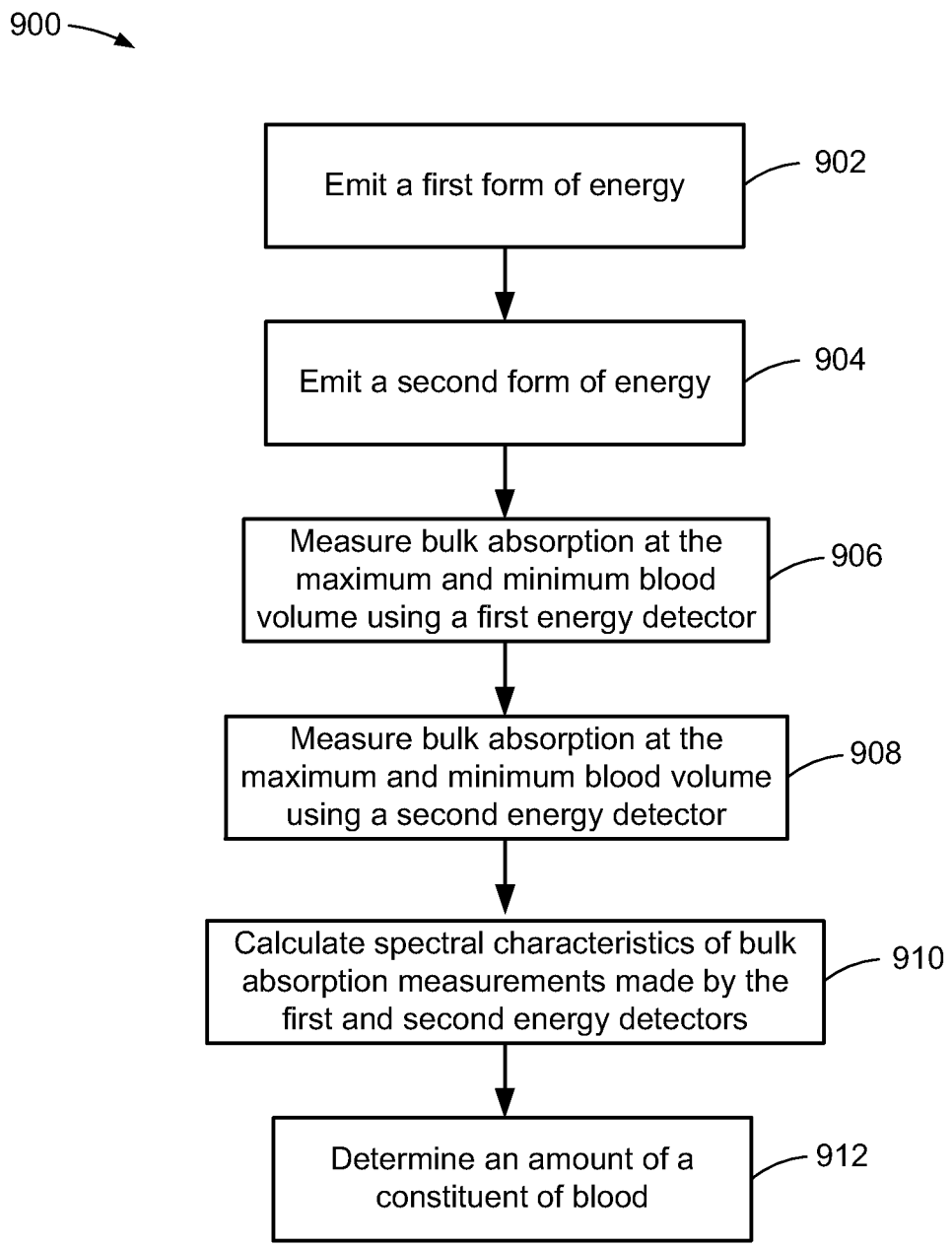
FIG. 9 uses a flow chart to illustrate a method for noninvasively measuring blood constituents in a subject in accordance with an example.

FIG. 9 uses a flow chart to illustrate a method for noninvasively measuring blood constituents in a subject. The method can comprise emitting a first form of energy at the subject, as in block 902. The method can further comprise emitting a second form of energy at the subject, as in block 904. The method can also comprise measuring bulk absorption by the subject of the first form of energy at the maximum and minimum blood volumes using a first energy detector, as in block 906. The method can also comprise measuring bulk absorption by the subject of the second form of energy at the maximum and minimum blood volumes using a second energy detector, as in block 908. The method can further comprise calculating, using a processor, spectral characteristics of bulk absorption measurements made by the first energy detector and the second energy detector, as in block 910. The method can further comprise determining, using the processor, an amount of at least one constituent of the blood, as in block 912.

Figure 10:
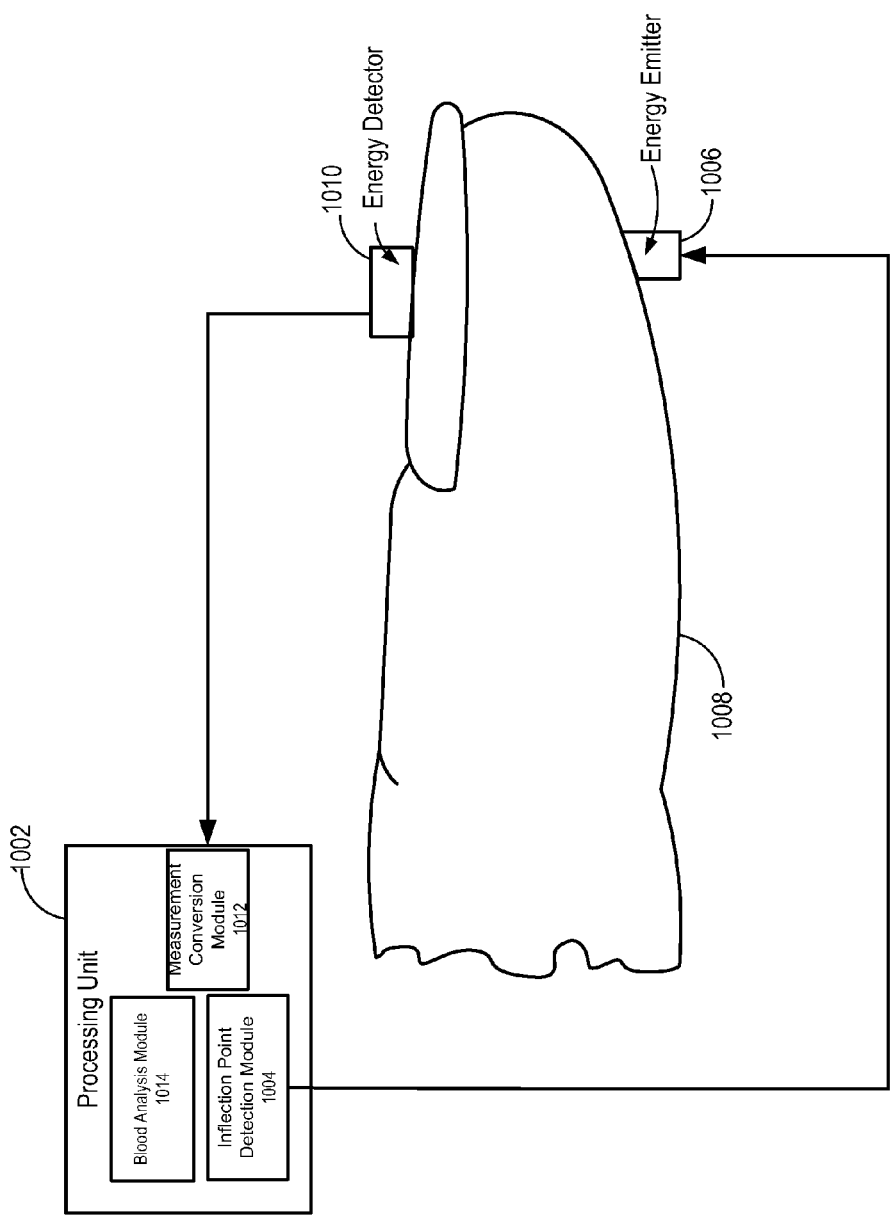
FIG. 10 is a schematic diagram of an system for noninvasive blood measurement in accordance with an example.

FIG. 10 uses a flow chart to illustrate a system for noninvasively measuring blood constituents in a subject. The system can comprise a processing unit 1002. The system may further comprise of an inflection point detection module 1004 configured to detect a maximum blood volume and a minimum blood volume. The system may also comprise an inflection point detection module 1004 configured to emit energy from an energy source using an energy emitter 1006 at the subject 1008 during the maximum blood volume and during the minimum blood volume. The system may also comprise a measurement conversion module 1012 configured to receive measurements of bulk absorption by the subject of the energy at the maximum and minimum blood volumes from an energy detector 1010. The system may also comprise a measurement conversion module 1012 configured to calculate spectral characteristics of the bulk absorption measurements received from the energy detector 1010. The system may also comprise a blood analysis module 1014 configured to determine an amount of at least one constituent of the blood.

Figure 11:
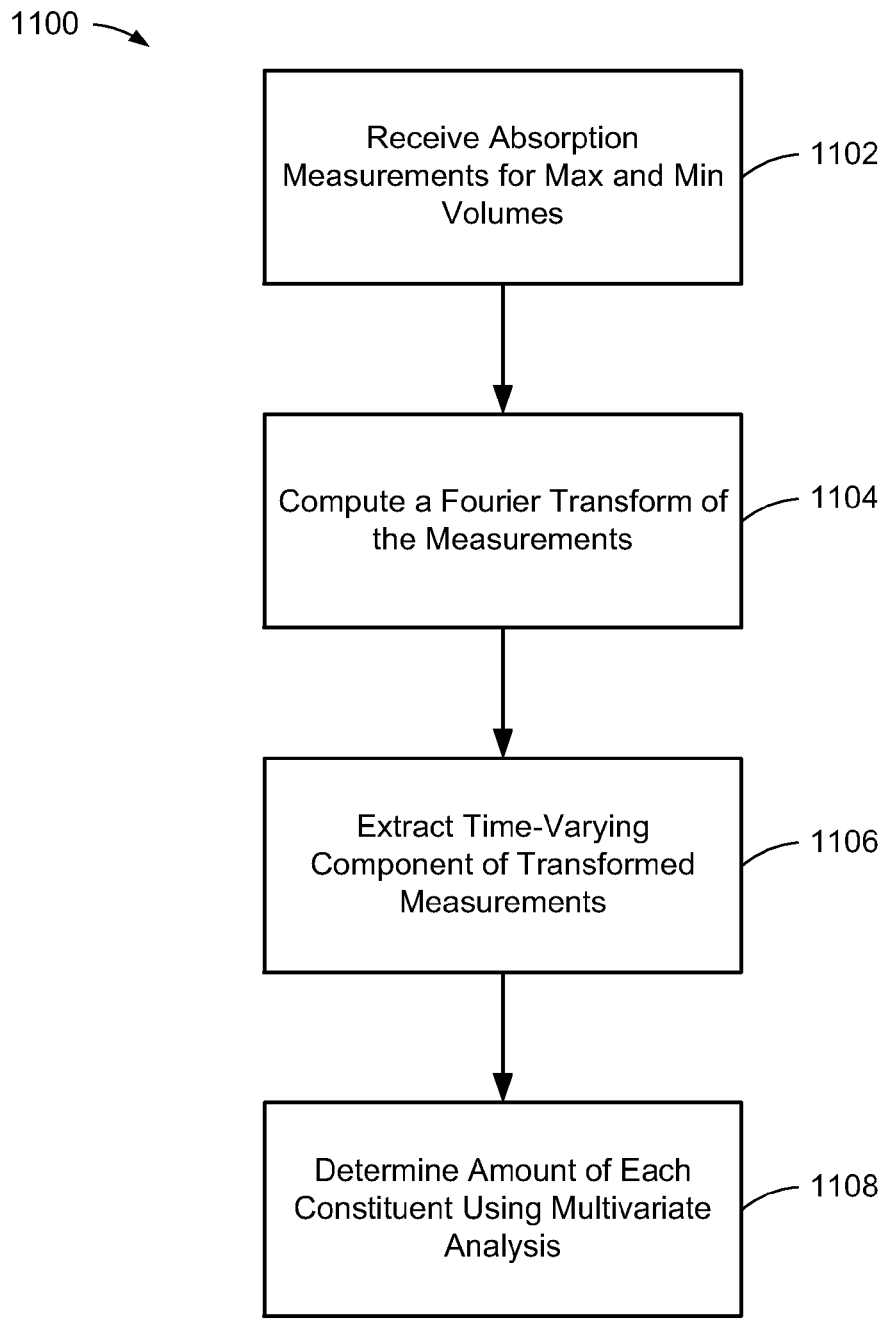
FIG. 11 uses a flow chart to illustrate a method for noninvasively measuring blood constituents in a subject in accordance with an example.

FIG. 11 is a flow diagram for a method 1100 of calculating the amount of each constituent in the blood from the bulk absorption measurements. Referring to FIG. 1, in one example embodiment the computer 140 may receive 1102 the bulk absorption measurements for the maximum and minimum blood volumes. For example, the bulk absorption measurements may have been temporarily stored in memory and retrieved therefrom, and/or the bulk absorption measurements may be received by the computer 140 from the spectrometer 130. The bulk absorption measurements may be, for example, a vector of bulk absorption measurements calculated from intensity measurements at a plurality of time points. The bulk absorption measurements for the maximum and minimum blood volumes may be received as part of a same communication, and/or the bulk absorption measurements for the maximum blood volume may be received separately from the bulk absorption measurements for the minimum blood volume.

The computer 140 may determine the bulk absorption measurements at a plurality of frequencies/wave lengths based on the received bulk absorption measurements. A Fourier transform of the bulk absorption measurements at the maximum blood volume may be computed independently of the Fourier transform of the bulk absorption measurements at the minimum blood volume. Accordingly, the computation 1104 may result in Fourier-transformed bulk absorption measurements for the maximum blood volume and Fourier-transformed bulk absorption measurements for the minimum blood volume. In an embodiment, the Fourier transform for the maximum and/or minimum blood volumes may be calculated while additional bulk absorption measurements for the maximum and/or minimum blood volumes have not yet occurred. Bulk absorption measurements may be made at a plurality of blood volume maximums and/or minimums, and a plurality of Fourier-transformed bulk absorption measurements for a plurality of blood volume maximums or minimums may be averaged to improve accuracy and/or precision. In alternate embodiments, the spectrometer 130 may compute 1104 the Fourier transform of the bulk absorption measurements before the computer 140 receives 1102 the Fourier-transformed bulk absorption measurements.

The computer 140 may extract 1106 a time-varying component from the Fourier-transformed bulk absorption measurements. The time-varying component may be determined by performing a comparison operation that compares the Fourier-transformed bulk absorption measurements at the maximum blood volume to the Fourier-transformed bulk absorption measurements at the minimum blood volume. In an embodiment, the comparison operation may include computing a difference between the Fourier-transformed bulk absorption measurements at individual wavelengths.

The computer 140 may determine 1108 the amount of each constituent of the blood by performing multivariate analysis on the time-varying component of the Fourier-transformed bulk absorption measurements. The bulk absorption coefficient of blood may be directly related to the bulk absorption coefficients of each constituent of the blood. A system of equations may be set up by performing the mathematical comparison operation at a plurality of different wavelengths. Using the known bulk absorption coefficients at each wavelength for each constituent of interest, a system of equations may be solved using multivariate analysis to calculate the amount (e.g., concentration) of each constituent of interest in the blood. The nature of blood is extremely complex comprised of a large number of proteins, fats, sugars, foreign substances and the like. For example a basic complete blood count (CBC) as often ordered by a practitioner is comprised of well over twenty individual parameters. Taken in aggregate blood is comprised of hundreds of substances in varying quantities. In many cases, however, only a relative handful of these substances are assayed to diagnose, monitor and treat an infirmity. Examples are red blood cell count (HCT) in the case of the anemia, white blood cell count in the case of infection, glucose levels in the case of diabetes management, and so on. The computer 140 may include an output device and may output the calculated amounts to a user. The calculated amounts may be updated as new measurements are made (e.g., by averaging measurements) and/or replaced as new measurements are made.

Figure 12:
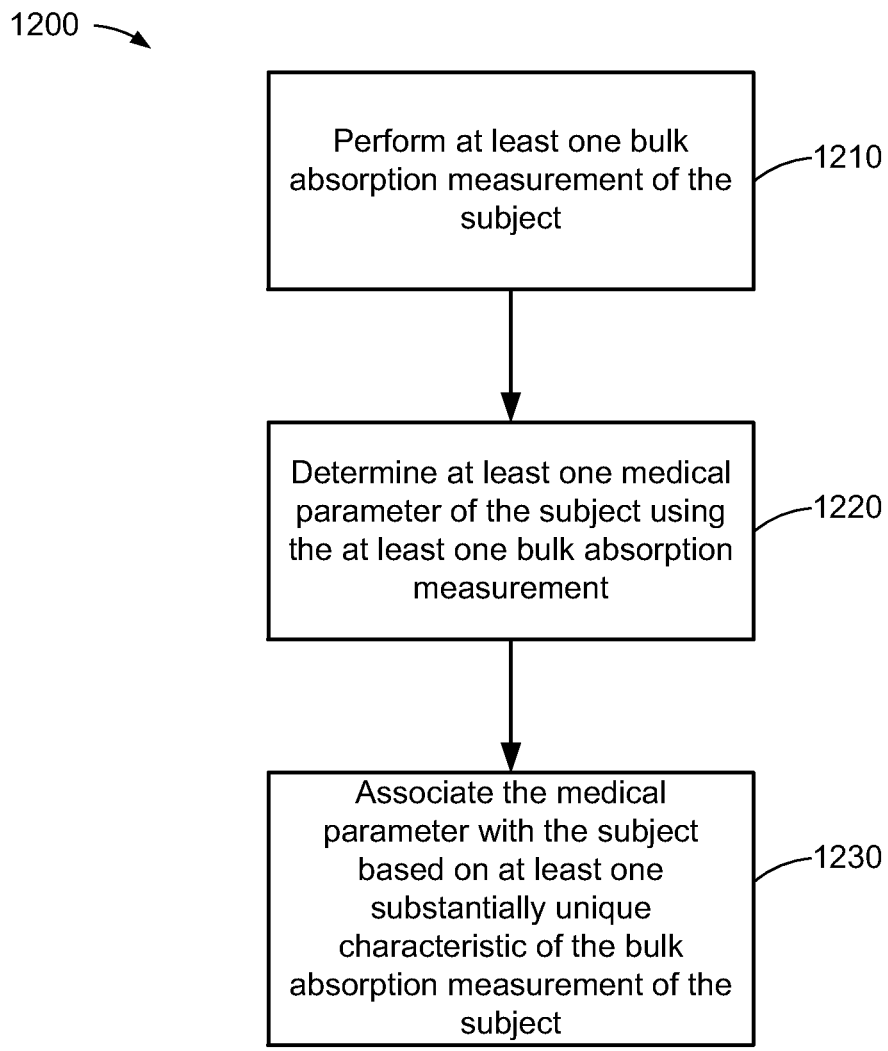
FIG. 12 depicts functionality of computer circuitry of a non-invasive biometric device operable to associate medical information with a subject in accordance with an example.

Another example provides functionality 1200 of computer circuitry of non-invasive biometric device operable to associate medical information with a subject, as shown in the flow chart in FIG. 12. The functionality may be implemented as a method or the functionality may be executed as instructions on a machine, where the instructions are included on at least one computer readable medium or one non-transitory machine readable storage medium. The computer circuitry can be configured to perform at least one bulk absorption measurement of the subject, as in block 1210. The computer circuitry can be further configured to determine at least one medical parameter of the subject using the at least one bulk absorption measurement, as in block 1220. The computer circuitry can be configured to associate the medical parameter with the subject based on at least one substantially unique characteristic of the bulk absorption measurement of the subject, as in block 1230.

In an example, the computer circuitry can be further configured to determine at least one identification parameter of the subject using the at least one bulk absorption measurement. In one example, the at least one identification parameter can includes at least one medical parameter. In another example, the computer circuitry can be further configured to identify the subject using the at least one identification parameter. In an example, the computer circuitry can be further configured to determine the at least one identification parameter or the at least one medical parameter using an analyzed form of the at least one bulk absorption measurement.

In one embodiment, the term medical parameter, as illustrated in the example of FIG. 12, can be a parameter that is identified and may be used in a medical analysis. The term identification parameter can be a medical parameter, but may also be a measured parameter that is not used in a medical analysis. For example, a hemoglobin measurement of a subject may be a medical parameter, while a skin color or skin translucency measurement may be used to identify a subject but may not have a medical use.

While specific embodiments and applications of the disclosure have been illustrated and described, it is to be understood that the disclosure is not limited to the precise configuration and components disclosed herein. Various modifications, changes, and variations apparent to those of skill in the art may be made in the arrangement, operation, and details of the methods and systems of the disclosure without departing from the spirit and scope of the disclosure. The scope of the present disclosure should, therefore, be determined only by the following claims.

Embodiments may include various steps, which may be embodied in machine-executable instructions to be executed by a computer system. A computer system includes one or more general-purpose or special-purpose computers (or other electronic devices). Alternatively, or in addition, the computer system may comprise hardware components that include specific logic for performing the steps or comprise a combination of hardware, software, and/or firmware. Without limitation, a computer system may comprise a workstation, laptop computer, disconnectable mobile computer, server, mainframe, cluster, so-called "network computer" or "thin client," tablet, smartphone, personal digital assistant or other hand-held computing device, "smart" consumer electronics device or appliance, or a combination thereof.

Each computer system includes at least a processor and a memory; computer systems may also include various input devices and/or output devices. The processor may include one or more general-purpose central processing units (CPUs), graphic processing units (GPUs), or Digital Signal Processors (DSPs), such as Intel®, AMD®, Nvidia®, ATI®, TIC), or other "off-the-shelf" microprocessors. The processor may include a special-purpose processing device, such as ASIC, PAL, PLA, PLD, Field Programmable Gate Array (FPGA), or other customized or programmable device. The memory may include static RAM, dynamic RAM, flash memory, ROM, CD-ROM, disk, tape, or magnetic, optical, or other computer storage medium. The input device(s) may include a keyboard, mouse, touch screen, light pen, tablet, microphone, sensor, or other hardware with accompanying firmware and/or software. The output device(s) may include a monitor or other display, printer, speech or text synthesizer, switch, signal line, or other hardware with accompanying firmware and/or software.

The computers may be capable of using a floppy drive, tape drive, optical drive, magneto-optical drive, memory card reader, or other means to read a storage medium. A suitable storage medium includes a magnetic, optical, or other computer-readable storage device having a specific physical configuration. Suitable storage devices include floppy disks, hard disks, tape, CD-ROMs, DVDs, PROMs, random access memory, flash memory, and other computer system storage devices. The physical configuration represents data and instructions which cause the computer system to operate in a specific and predefined manner as described herein.

Embodiments may also be provided as a computer program product, including a non-transitory machine-readable storage medium having stored thereon instructions that may be used to program a computer (or other electronic device) to perform processes described herein. The non-transitory machine-readable storage medium may include, but is not limited to, hard drives, floppy diskettes, optical disks, CD-ROMs, DVD-ROMs, ROMs, RAMs, EPROMs, EEPROMs, magnetic or optical cards, tapes, solid-state memory devices, or other types of media/machine-readable media suitable for storing electronic instructions.

Suitable software to assist in implementing the invention is readily provided by those of skill in the pertinent art(s) using the teachings presented here and programming languages and tools, such as Java, Pascal, C++, C, PHP, JavaScript, Python, C#, Perl, SQL, Ruby, Shell, Visual Basic, Assembly, Action Script, Objective C, Lisp, Scala, Tcl Haskell, Scheme, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

Several aspects of the embodiments described will be illustrated as software modules or components. As used herein, a software module or component may include any type of computer instruction or computer-executable code located within a memory device. A software module may, for instance, comprise one or more physical or logical blocks of computer instructions, which may be organized as a routine, a program, a script, an object, a component, a data structure, etc., which performs one or more tasks or implements particular abstract data types.

In certain embodiments, a particular software module may comprise disparate instructions stored in different locations of a memory device, different memory devices, or different computers, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Much of the infrastructure that may be used according to the present invention is already available, such as general-purpose computers, computer programming tools and techniques, computer networks and networking technologies, and digital storage media.

The invention claimed is:

1. An apparatus for noninvasive measurement of blood constituents, the apparatus comprising:
   a broad-spectrum light source configured to emit first light having a broad spectrum at a subject;
   a broad-spectrum light detector configured to acquire absorption measurements, comprising:
      a first measurement of a bulk absorption by the subject of the first light emitted by the broad-spectrum light source at a maximum blood volume, and
      a second measurement of a bulk absorption by the subject of the first light emitted by the broad-spectrum light source at a minimum blood volume;
   a narrow-spectrum light source configured to emit a second light having a narrow spectrum at the subject;
   a narrow-spectrum light detector configured to acquire absorption measurements, comprising:
      a third measurement of a bulk absorption by the subject of the second light emitted by the narrow-spectrum light source at the maximum blood volume, and
      a fourth measurement of a bulk absorption by the subject of the second light emitted by the narrow-spectrum light source at the minimum blood volume;
   a processor configured to:
      receive the first measurement and the second measurement from the broad-spectrum light detector,
      receiving the third measurement and the fourth measurement from the narrow-spectrum light detector,
      determine a first value representing an orthogonality between the first measurement of the bulk absorption by the subject of the first light emitted by the broad-spectrum light source at the maximum blood volume and the third measurement of the bulk absorption by the subject of the second light emitted by the narrow-spectrum light source at the maximum blood volume,
      determine a second value representing an orthogonality between the second measurement of the bulk absorption by the subject of the first light emitted by the broad-spectrum light source at the minimum blood volume and the fourth measurement of the bulk absorption by the subject of the second light emitted by the narrow-spectrum light source at the minimum blood volume,
      determine an amount of at least one blood constituent using the first value and the second value.

2. The apparatus of claim 1, wherein the broad spectrum light detector is further configured to continuously measure bulk absorption by the subject of the first light emitted by the broad-spectrum light source.

3. The apparatus of claim 1, wherein the processor is further configured to calculate spectral characteristics of the first measurement, the second measurement, the third measurement, and the fourth measurement.

4. The apparatus of claim 3, wherein calculating the spectral characteristics comprises:
   calculating a frequency transform of the first measurement, second measurement, third measurement, and the fourth measurement; and
   extracting a time-varying component of the frequency transform of the first measurement, second measurement, third measurement, and the fourth measurement.

5. The apparatus of claim 4, wherein extracting the time-varying component comprises performing a mathematical comparison operation between the frequency-transformed first measurement and frequency-transformed third measurement, and a mathematical comparison operation between the frequency-transferred second measurement and the frequency-transformed fourth measurement.

6. The apparatus of claim 5, wherein performing the mathematical comparison operation between the frequency-transformed first measurement and frequency-transformed third measurement comprises calculating one or more of a difference and a ratio between at least one point in the frequency-transformed first measurement and the frequency-transformed third measurement, and
   wherein performing the mathematical comparison operation between the frequency-transformed second measurement and frequency-transformed third measurement comprises calculating one or more of a difference and a ratio between at least one point in the frequency-transformed second measurement and the frequency-transformed fourth measurement.

7. The apparatus of claim 4, wherein determining the amount of the at least one constituent of the blood comprises performing multivariate analysis of the time-varying component of one or more of the frequency-transformed first measurement, the frequency-transformed second measurement, the frequency-transformed third measurement, and the the frequency-transformed fourth measurement.

* * * * *